(12) United States Patent
Wang

(10) Patent No.: US 8,570,511 B2
(45) Date of Patent: Oct. 29, 2013

(54) WIDE SIZE RANGE FAST INTEGRATED MOBILITY SPECTROMETER

(75) Inventor: Jian Wang, Setauket, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 398 days.

(21) Appl. No.: 12/877,677

(22) Filed: Sep. 8, 2010

(65) Prior Publication Data

US 2011/0116092 A1    May 19, 2011

Related U.S. Application Data

(60) Provisional application No. 61/240,788, filed on Sep. 9, 2009.

(51) Int. Cl.
*G01N 15/02* (2006.01)

(52) U.S. Cl.
USPC .......................................................... 356/335

(58) Field of Classification Search
USPC ................................................... 356/300–334
See application file for complete search history.

(56) References Cited

U.S. PATENT DOCUMENTS

| | | | | |
|---|---|---|---|---|
| 5,922,976 | A | 7/1999 | Russell et al. | 73/865.5 |
| 6,003,389 | A | 12/1999 | Flagan et al. | 73/865.5 |
| 6,259,101 | B1 | 7/2001 | Wexler et al. | 250/423 |
| 6,263,744 | B1 | 7/2001 | Russell et al. | 73/865.5 |
| 7,298,486 | B2 * | 11/2007 | Wang et al. | 356/438 |
| 2008/0073503 | A1 * | 3/2008 | Wu | 250/283 |

OTHER PUBLICATIONS

"Differential Mobility Analyzer," Aerosol Physics: Focusing in Processes, ITM, Stockholm University, Nov. 7, 2007.
Olfert et al., "Dynamic Characteristics of a Fast-Response Aerosol Size Spectrometer," Atmos. Sci. Technol., Sep. 2008, available at http://www.ecd.bnl.gov/pubs/BNL-90041-2008-JA.pdf.
Wang, "A Fast Integrated Mobility Spectrometer with Wide Dynamic Size Range: Theoretical Analysis and Numerical Simulation," Aerosol Science, Jun. 2009, pp. 890-906, available at http://www.ecd.bnl.gov/pubs/BNL-82343-2009-JA.pdf.
Wang, "A Fast Integrated Mobility Spectrometer for Rapid Measurement of Aerosol Size Distribution," Instrumentation Workshop 2008, Atmospheric Radiation Measurement, U.S. Department of Energy, Oct. 14, 2008, available at http://www.arm.gov/sites/aaf/workshop2008; http://www.arm.gov/sites/aaf/workshop2008/1014/1130to1145Wang.pdf.
Wang, "A Fast Integrated Mobility Spectrometer with Enhanced Dynamic Size Range," Science Team Meeting, Atmospheric Science Program, U.S. Department of Energy, Feb. 27, 2009, available at http://www.asp.bnl.gov/ASP_STmtgFY2009Program.html; http://www.asp.bnl.gov/ASP_ST_mtg_pres_2009/WangFIMS_ASP2009.pdf.

* cited by examiner

*Primary Examiner* — Tara S Pajoohi Gomez
(74) *Attorney, Agent, or Firm* — Dorene M. Price

(57) ABSTRACT

A mobility spectrometer to measure a nanometer particle size distribution is disclosed. The mobility spectrometer includes a conduit and a detector. The conduit is configured to receive and provide fluid communication of a fluid stream having a charged nanometer particle mixture. The conduit includes a separator section configured to generate an electrical field of two dimensions transverse to a dimension associated with the flow of the charged nanometer particle mixture through the separator section to spatially separate charged nanometer particles of the charged nanometer particle mixture in said two dimensions. The detector is disposed downstream of the conduit to detect concentration and position of the spatially-separated nanometer particles.

30 Claims, 10 Drawing Sheets

WIDE SIZE RANGE FAST INTEGRATED MOBILITY SPECTROMETER

CROSS-REFERENCE TO RELATED APPLICATIONS

This application claims the benefit of U.S. Provisional Application No. 61/240,788, filed Sep. 9, 2009, which is incorporated herein by reference in its entirety.

STATEMENT OF GOVERNMENT RIGHTS

This invention was made with Government support under contract number DE-AC02-98CH10886, awarded by the United States Department of Energy. The Government has certain rights in the invention.

BACKGROUND OF THE INVENTION

The present application relates generally to mobility spectrometers for measuring particle size distributions in fluid streams. More specifically, the present application is directed to a fast integrated mobility spectrometer, spectrometer and method of measuring participle size distributions of a wide size range.

Real-time measurement of particle size distributions, especially in the nanometer size range, is important in many applications such as measurement of atmospheric aerosols and characterization of particles in combustion systems. Rapid measurements are often required to capture transient aerosol dynamics occurring on very small time scales, such as in high temperature environments or other nucleation-dominated systems. In other types of measurements, such as those onboard fast-moving platforms (e.g., research aircraft) aimed at characterizing spatial and temporal distributions of atmospheric aerosols, high time resolution is essential to capture the variations of aerosol properties over small spatial domain.

Currently, sub-micrometer aerosol size distributions are often measured using a Scanning Mobility Particle Sizer ("SMPS"). The SMPS is a sequential measurement technique. Therefore, only particles within a narrow size range, which represent a small fraction of total particles introduced, are measured at one time. Obtaining the entire aerosol size distribution requires scanning the classifying voltage over a wide range, which typically takes about one minute and is too slow for aircraft-based measurements. The time required for scanning the classifying voltage can be reduced by using a fast-response detector (e.g., mixing-type condensation nucleus counter). However, because only a small fraction of total particles is measured at a time, the sampling rate of the SMPS is insufficient for rapid measurements. As a result, despite the improvement in measurement speed by using the fast-response detector, measurements in clean environments are often compromised by the time required to obtain statistically significant numbers.

Other mobility-based instruments have been used to measure particles of different mobilities simultaneously. For example, Electrical Aerosol Spectrometer ("EAS"), Engine Exhaust Particle Sizer ("EEPS") and Differential Mobility Spectrometer ("DMS") have been used to measure particles of different mobilities simultaneously using an array of integrated electrometers, capable of sub-second measurements of aerosol size distributions. However, due to the low sensitivity of the electrometers, applications of these instruments are limited to aerosols with high number concentrations, such as engine exhausts. Besides low sensitivity, the EAS, EEPS, and DMS also have a considerably lower size resolution than does the SMPS.

Another instrument frequently used to measure sub-micrometer aerosol size distributions is an Optical Particle Counter ("OPC"), which measures particle sizes based on the intensity of light scattered by the particles. The OPC offers fast measurement speed and better counting statistics than does SMPS, but its measurement range is usually limited to particles with diameters greater than 100 nm. In addition, particle physical properties such as shape, refractive index, and morphology have strong influences on derived particle sizes, and are often unavailable. Even for the ideal case of homogeneous spherical aerosol particles, the uncertainty in refractive index often leads to significant uncertainties in derived size distributions.

A Fast Integrated Mobility Spectrometer ("FIMS") has been developed previously to measure particles of different mobilities simultaneously. See U.S. Pat. No. 7,298,486 to Wang, et al. The disclosure of the '486 patent is incorporated herein by reference in its entirety. The simultaneous measurement of particles with different sizes/mobilities provides size spectra of sub-micrometer aerosol at a time resolution of 1 Hz, nearly 100 times faster than traditional SMPS. Since individual particles and their mobility dependent positions are detected optically using a high resolution CCD camera, the FIMS also offers high size resolution and counting statistics. While the FIMS is capable of rapid measurements, it has a relatively narrower dynamic size range compared to SMPS. To achieve good size resolution, the measurement range of a single FIMS is limited to about a decade in electrical mobility. For the measurements of sub-micrometer size distribution ranging from about 15 nm to about 1000 nm, three FIMS can be operated in parallel, with each of the FIMS operating at a different separating voltage and covering a fraction of the total size range.

SUMMARY OF THE INVENTION

In accordance with an embodiment of the present invention, a mobility spectrometer to measure a nanometer particle size distribution is disclosed. The mobility spectrometer includes a conduit with a separator section configured to generate an electrical field of two dimensions transverse to a dimension associated with the flow of a charged nanometer particle mixture through the separator section to spatially separate charged nanometer particles of the charged nanometer particle mixture in the two dimensions. The conduit receives and provides fluid communication to a fluid stream of the charged nanometer particle mixture. The spectrometer includes a detector that is disposed downstream of the conduit to detect concentration and position of the spatially-separated nanometer particles.

In accordance with another embodiment of the present invention, a mobility spectrometer system to measure a nanometer particle size distribution is disclosed. The mobility spectrometer system includes a charger and a mobility spectrometer. The charger is configured to receive a first fluid stream of nanometer particles and to charge said nanometer particles. The charger is further configured to direct the first fluid stream into a conduit of the mobility spectrometer. The mobility spectrometer is in fluid communication with the charger and includes a conduit and a detector. The conduit is configured to receive the first fluid stream. The conduit includes a separator section to generate an electrical field of two dimensions transverse to a dimension associated with the flow of the first fluid stream through the separator section to separate charged nanometer particles of the fluid stream in the two dimensions. The detector is disposed downstream of the conduit to detect concentration and position of said spatially-separated nanometer particles.

In accordance with the present invention, a method of measuring a nanometer particle size distribution is also provided. A fluid stream having a charged nanometer particle mixture is flowed through a conduit of a mobility spectrometer. The conduit includes at least a separator section. An electrical field of two dimensions is applied in the separator section transverse to a dimension associated with the flow of the charged nanometer particle mixture through the conduit to spatially separate charged nanometer particles of the charged nanometer particle mixture in the two dimensions. The concentration and position of the spatially-separated nanometer particles are detected.

The mobility spectrometer, system and method increase the size range of measurable particle sizes to between about 10 nm and 1470 nm, mitigating the necessity of operating multiple measurement instruments in parallel to achieve the measurable size range.

For a more thorough understanding of the present invention, reference is made to the following description, taken in conjunction with the accompanying drawings, and its scope will be pointed out in the appended claims.

BRIEF DESCRIPTION OF THE DRAWINGS

Some embodiments are illustrated by way of example and not limitation in the figures of the accompanying drawings in which.

DETAILED DESCRIPTION

A wide size range fast integrated mobility spectrometer ("WSR-FIMS"), a WSR-FIMS system and a method of measuring nanometer particle size distributions are described. A framework is developed to derive a transfer function, resolution, and transmission efficiency of the WSR-FIMS system. Two representative operation configurations are simulated to demonstrate that the WSR-FIMS system increases the size range of measurable particle sizes to between about 10 nm and 1470 nm. In the following description, for the purposes of explanation, numerous specific details are set forth in order to provide a thorough understanding of example embodiments.

Figure 1:
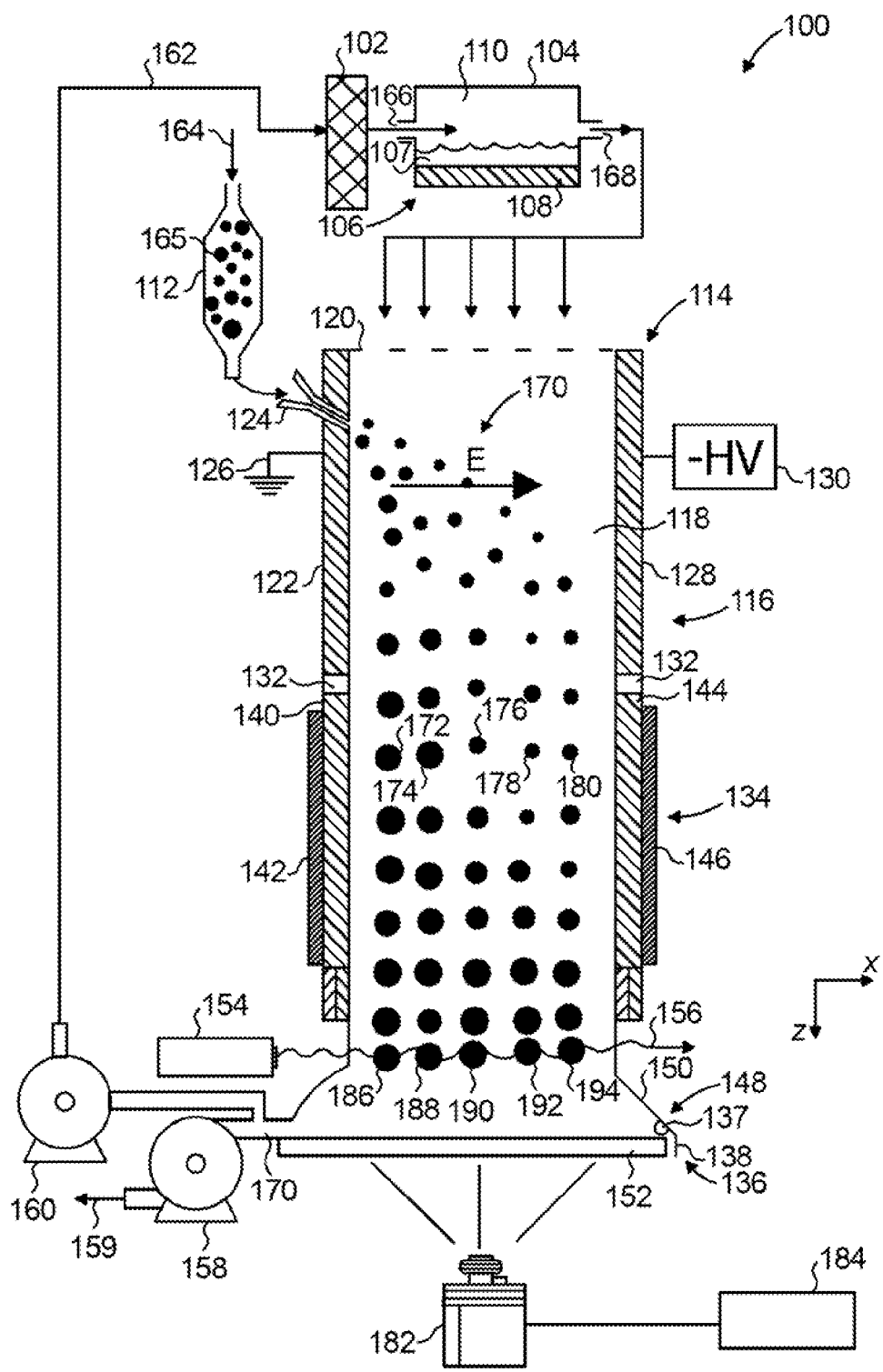
FIG. 1 illustrates an elevated cross-section of an example wide size range fast integrated mobility spectrometer ("WSR-FIMS") system configured to measure a nanometer particle size distribution in a range from about 10 nm to about 1470 nm.

FIG. 1 illustrates an elevated cross-section of an example wide size range fast integrated mobility spectrometer ("WSR-FIMS") system 100 configured to measure a nanometer particle size distribution of a wide size range, such as, a nanometer particle size distribution from about 10 nm to about 1470 nm. The WSR-FIMS system 100 includes a filter 102, a saturator 104, a charger 112, a mobility spectrometer 114, a light source 154, a pump 158, a regenerative blower 160, and a computing device 184.

The filter 102 is configured to receive a first fluid stream 162 and to substantially eliminate all particles that may be present in the first fluid stream 162. For example, the filter may be a high-efficiency particulate air ("HEPA") filter that substantially eliminates all particles from the first fluid stream 162.

The saturator 104 is in fluid communication with the filter 102 and with the mobility spectrometer 114. The saturator 104 is configured to saturate the first fluid stream 162, received after passing through the filter 102, with a condensing agent 107 and further configured to direct the first fluid stream 162 into the mobility spectrometer 114. The saturator 104 includes an inlet 166, an outlet 168, a reservoir 106 and a heater 108. The first fluid stream 162 that is received from the filter 102 enters the saturator 104 through the inlet 166 and exits the saturator 104 through outlet 168. The reservoir 106 holds the condensing agent 107 that—upon being heated by the heater 108 forms a vapor 110—saturates the first fluid stream 162 as the first fluid stream 162 travels through the saturator 104. The first fluid stream 162 can be introduced into the mobility spectrometer 114 at a flow rate of about 15.0 L/min. The flow rate may be driven or controlled by the regenerative blower 160 operatively connected to the mobility spectrometer 114 and the filter 102. Specifically, the regenerative blower 160 re-circulates a portion of mixture 170 exiting from the mobility spectrometer 114 through the filter 102 and the saturator 104 back to the mobility spectrometer 114.

The charger 112 is in fluid communication with the mobility spectrometer 114. The charger 112 is configured to receive a second fluid stream 164 and to charge nanometer particles 165 in the second fluid stream 164 with an electrical charge. The second fluid stream 164 can flow through the charger 112 and be introduced into the mobility spectrometer 114 at a flow rate of about 0.3 L/min. The flow rate may be driven or induced by the pump 158 operatively connected to the mobility spectrometer 114.

The mobility spectrometer 114 is in fluid communication with the saturator 104 and the charger 112 to receive the first fluid stream 162 and the second fluid stream 164, respectively, forming a charged nanometer particle mixture 170 entrained in the mobility spectrometer 114. The mobility spectrometer 114 is configured to measure particle size distribution of charged nanometer particles 165 in the nanometer particle mixture 170 having different nanometer sizes between about 10 nm and about 1470 nm.

The mobility spectrometer 114 includes a conduit 118 and a detector 182. The conduit 118 is configured to receive the first fluid stream 162, through a first inlet 120 (disposed on a top of the conduit 118) and the second fluid stream 164 through a second inlet 124 (disposed on a side of the conduit 118) and further configured to provide fluid communication of the resultant charged nanometer particle mixture 170 out of the conduit 118. The conduit 118 includes a separator section 116 and a condenser section 134 that are electrically separated (e.g., by couplers or flanges 132) and an outlet 148. The outlet 148 is downstream from the inlets 120, 124.

The separator section 116 of the conduit 118 is configured to spatially separate the charged nanometer particles 165 in the nanometer particle mixture 170 entrained in the conduit 118 into particles having different nanometer sizes between about 10 nm and about 1470 nm. The separator section 116 includes a first plate electrode 122 that is disposed in parallel to an opposing second plate electrode 128. The first plate electrode 122 is connected to ground 126, while a negative voltage source 130 is applied to the second plate electrode 128. The negative voltage source 130 is configured to apply non-uniform or varying voltages (e.g., linearly, exponentially) across the width of the opposing second plate electrode 128, from about −28 volts to about −11,000 volts. The varying voltages induce or generate multiple electric fields in the conduit 118 that are transverse to the flow of the charged nanometer particle mixture 170 through the conduit 118. The flow of the charged nanometer particle mixture 170 is in a z-dimension. The generated electric fields can be described as a non-uniform electric field E. More specifically, the generated electric fields can be described by an electric field E of two dimensions, the x- and y-dimensions. The electric field E is non-uniform across both the x- and y-dimensions. For example, the first dimension (e.g., x-dimension) of the electric field E is between the first plate electrode 122 and the second plate electrode 128. The second dimension (e.g., y-dimension) of the electric field E is across the width of the opposing second plate electrode 128. The non-uniformity of the electric field E in both dimensions results from the first plate electrode 122 at ground and the non-uniform voltages across the width of the opposing second plate electrode 128. The electric field E (in the x- and y-dimensions) is transverse to the flow of the charged nanometer particle mixture 170 through the conduit 118 in the z-dimension.

Under the influence of the electric fields E, charged nanometer particles 165 of the charged nanometer particle mixture 170 are spatially separated by size into two dimensions (e.g., x- and y-dimensions) for particles with sizes between about 10 nm and about 1470 nm. The spatial separation is based on the particles' electrical mobility induced by the transverse electrical field E. More specifically, the smaller and more mobile particles move faster in the direction of the electric field E than the larger and less mobile particles. The smaller particles migrate farther toward the opposing second plate electrode 128 and farther toward the stronger portions of the electrical field E across the width of the second plate electrode 128. For example, the particles 172, 174, 176, 178 and 180 are spatially separated by size into two dimensions of particles that have different nanometer sizes between about 10 nm and about 1470 nm. It should be noted that the particles 172, 174, 176, 178 and 180 represent an example number of particles and that a multiplicity of particles would be spatially separated by size in the charged nanometer particle mixture 170.

The condenser section 134 of the conduit 118 is configured to condense the condensing agent in the charged nanometer particle mixture 170 to grow the spatially separated particles in the charged nanometer particle mixture 170 for detection. The condenser section 134 is disposed downstream from the separator section 116 and includes a first conductive plate 140 that is disposed in parallel to an opposing second conductive plate 144, both plates being connected to ground. The first conductive plate 140 is connected to a first thermoelectric cooler 142 and the second opposing conductive plate 144 is connected to a second thermoelectric cooler 146. The thermoelectric coolers 142, 146 are configured to cool the spatially-separated charged nanometer particle mixture 170 within the conduit 118. The spatially-separated charged nanometer particle mixture 170 is cooled to about 5° C. The cooling causes the condensing agent 107 (e.g., the condensing agent vapor 110) to condense on the nuclei of the spatially-separated particles, forming micrometer droplets. For example, the condenser section 134 grows the spatially-separated particles 172, 174, 176, 178, 180 into spatially-separated and grown micrometer droplets 186, 188, 190, 192 and 194. It should be noted that the micrometer droplets 186, 188, 190, 192 and 194 represent an example number of droplets and that a multiplicity of micrometer droplets are grown from the spatially-separated nanometer particles in the charged nanometer particle mixture 170.

The outlet 148 of the conduit 118 is configured to facilitate the detection and exit of the spatially-separated and grown micrometer droplets from the mobility spectrometer 114. In regard to the exit, the pump 158 facilitates the exhaust of a portion 159 of the spatially-separated charged nanometer particle mixture 170 from the conduit 118, while the regenerative blower 160 re-circulates a portion 162 of the spatially-charged nanometer particle mixture 170 through the filter 102 and the saturator 104 back to the mobility spectrometer 114. The outlet 148 includes a hood 150, a transparent window 152 and a condensation remover 136. The transparent window 152 facilitates detection by the detector 182. The condenser section 134 is substantially lower than ambient temperature, while the outlet 148 (e.g., hood 150 and transparent window 152) is close to ambient temperature. Because the temperature of the outlet 148 is substantially higher than the temperature of condenser section 134, a large fraction of the micrometer droplets 186, 188, 190, 192 and 194 will evaporate in the outlet 148 and will return to nanometer particles after detection by detector 182.

The condensation remover 136 of the outlet 148 is configured to remove excess condensation that may accumulate in the conduit 118. The condensation remover 136 includes a groove 137 in the hood 150 and a condensation outlet 138 through the transparent window 152. Excess condensation is drawn downwardly under the influence of gravity via the groove 137 and out of the conduit 118 via the condensation outlet 138. A peristaltic pump (not shown) can be used to facilitate removal of the condensation via the condensation outlet 138.

The detector 182 of the mobility spectrometer 114 is disposed downstream of the condenser section 134 and proximately to the transparent window 152 of the outlet 148. The detector 182 is configured to detect the concentration and position of the spatially-separated grown micrometer droplets (e.g., micrometer droplets 186, 188, 190, 192, 194) through the transparent window 152 of the hood 150 via one or more images. The detector 182 can be a high-speed digital camera that optically detects the concentration and position of the spatially-separated grown micrometer droplets. The camera can include a lens and frame transfer CCD. The frame transfer CCD can have an active area of about 12.3 mm×12.3 mm, consisting of 1024×1024 pixels, wherein each pixel is 12 μm×12 μm. The lens can have a magnification ratio of 0.205 and projects a 6 cm×1 cm viewing area on an area of 1.23 cm×0.205 cm (1024×171=175,104 pixels) on the CCD. This arrangement can produce a spot size of the particle image that is less than 24 μm in diameter, which is about 4 pixels (2×2) on the CCD. The camera can be operated at a readout speed of 10-60 fps to mitigate the probability of the camera detecting multiple micrometer droplets at the same location.

The light source 154 of the WSR-FIMS system 100 is disposed proximately to the condenser section 134 and configured to illuminate the spatially-separated grown micrometer droplets (e.g., micrometer droplets 186, 188, 190, 192, 194) to facilitate detection of the micrometer droplets by the detector 182 through the transparent window 152. The light source 154 can be configured to direct a collimated sheet of light 156 perpendicularly to the flow of the spatially-separated grown micrometer droplets, illuminating the micrometer droplets as they cross the sheet of light 156. The cross-section of the sheet of light 156 after collimation is about 1 cm×1 mm. The light source 154 is configured to illuminate the grown micrometer droplets for about 3 milliseconds as they cross the 1 mm sheet of light sheet 156.

The computing device 184 of the WSR-FIMS system 100 is operably connected to the detector 182. The computing device 184 can include a storage medium storing instructions executable by a processor configured to determine the concentration of the grown micrometer droplets detected by the detector 182. Specifically, the computing device 184 can determine the nanometer particle size distribution (concentrations and positions) of the charged nanometer particles 165 in the nanometer particle mixture 170 having different nanometer sizes between about 10 nm and about 1470 nm based on positions of the micrometer droplets.

Figure 2:
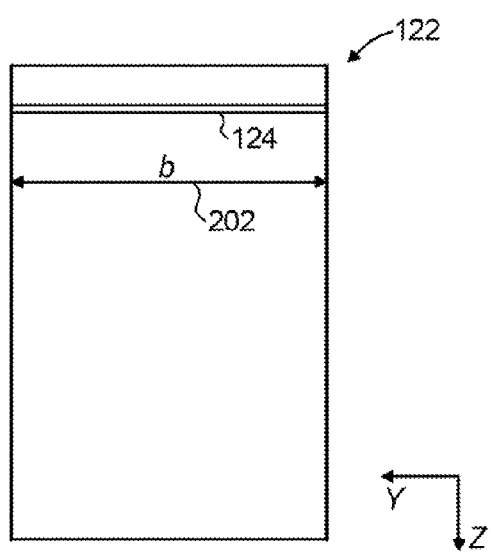
FIG. 2 illustrates the first plate electrode of the separator section 116 illustrated in FIG. 1.

FIG. 2 illustrates the first plate electrode 122 of the separator section 116 illustrated in FIG. 1. As particularly illustrated in FIG. 2, the first plate electrode 122 has a width 202 of about 10 cm and a length of about 25 cm. The first plate electrode 122 also includes the second inlet 124 to receive the second fluid stream 164 into the conduit 118 of the mobility spectrometer 114. The second inlet 124 can be a narrow slit substantially along its entire width of the first plate electrode 122.

Figure 3:
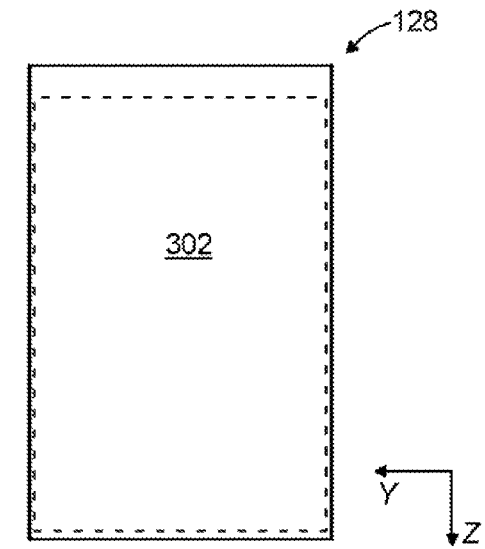
FIG. 3 illustrates second plate electrode of the separator section 116 illustrated in FIG. 1.

FIG. 3 illustrates second plate electrode 128 of the separator section 116 illustrated in FIG. 1. The second plate electrode 128 has substantially the same width and length as the first plate electrode 122 illustrated in FIG. 2. As particularly illustrated in FIG. 2, the second plate electrode 128 includes at least one electrical element 302 disposed substantially along the length and the width of the first plate electrode 128 and configured to provide a non-uniform voltage (e.g., linearly, exponentially) across the width of the second plate electrode 128, from about −28 volts to about −11,000 volts. As described in reference to FIG. 1 above, the non-uniform voltage induces a non-uniform electric field E in the conduit 118 that is perpendicular to and varies across the flow of the charged nanometer particle mixture 170 through the conduit 118.

Figure 4:
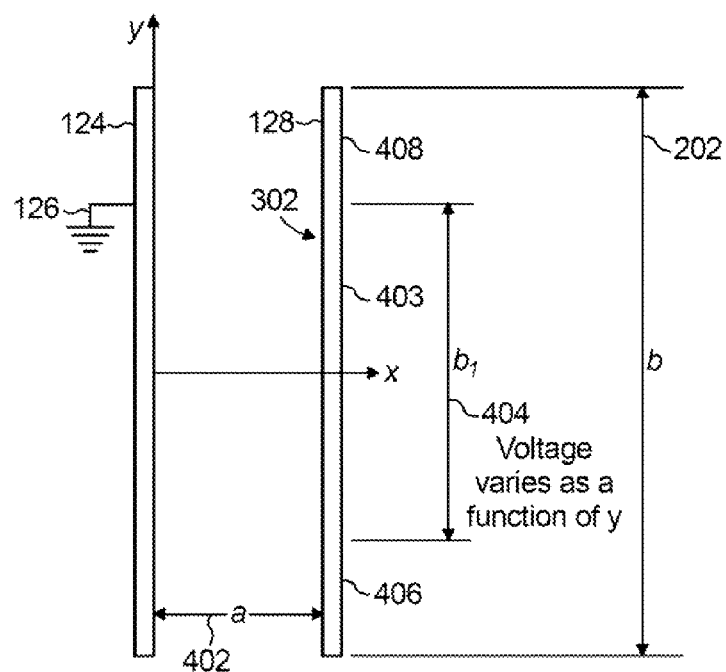
FIG. 4 illustrates a transverse cross-section of a first example embodiment of the second plate electrode illustrated in FIG. 3.

FIG. 4 illustrates a transverse cross-section of a first example embodiment of the second plate electrode 128 illustrated in FIG. 3. As illustrated in FIG. 4, the distance a 402 between the first plate electrode 124 and the second plate electrode 128 is approximately 1 cm. The first plate electrode 124 is set to ground. The second plate electrode 128 (via at least one electrical element 302) is configured to provide a non-uniform electrical field that is transverse to the flow of the charged nanometer particle mixture 170. More specifically, varying voltages (linear, exponential) provided across the width 202 of the second plate electrode 128, from about −28 volts to about −11,000 volts generate a non-uniform electrical field of two dimensions. The dimensions of the non-uniform electrical field are transverse to the dimension of the flow of the charged nanometer particle mixture 170. For example, the first dimension (e.g., x-dimension) of the electric field is between the first plate electrode 122 and the second plate electrode 128. The second dimension (e.g., y-dimension) of the electric field is across the width of the opposing second plate electrode 128. In one example of generating the non-uniform electrical field, the second plate electrode 128 is set to a first voltage (e.g., about −28 volts) at a first portion 406 along the width 202 and set to a second voltage (e.g., such as −11,000 volts) at a second portion 408 along the width 202. The second plate electrode 128 is further configured to provide a non-uniform voltage at a central portion 403, such as between about −28 volts and about −11,000 volts, the voltage rising linearly or exponentially along the width 404 of the second plate electrode 128.

In the second plate electrode 128, each of one or more parts of the central portion 403 can be set to a rising voltage between about −28 volts and about −11,000 volts. For example, a first part of the central portion 403 can be set to a first voltage, a second part of the central portion 403 can be set to a second voltage that is higher than the first voltage; a third part of the central portion 403 can be set to a third voltage that is higher than the second voltage, and so on.

Figure 5:
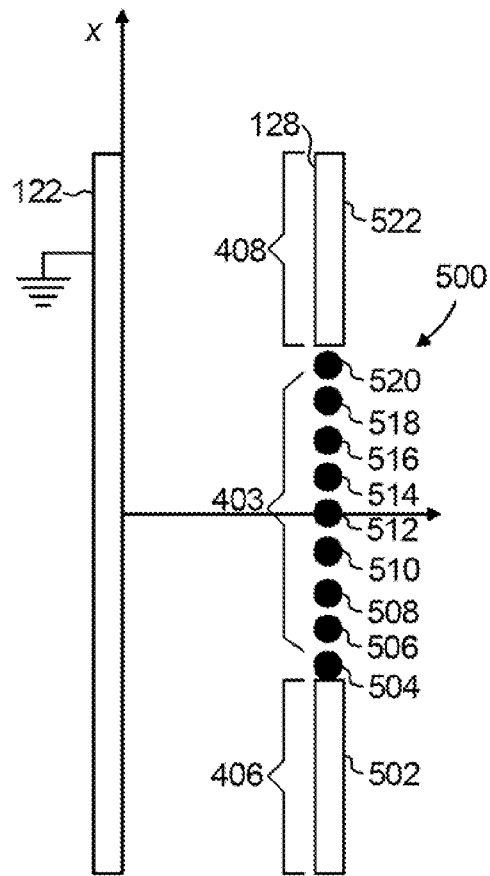
FIG. 5 illustrates a transverse cross-section of a second example embodiment of the second plate electrode illustrated in FIG. 3.

FIG. 5 illustrates a cross-section of a potential configuration of the second plate electrode 128 illustrated in FIG. 3. The second plate electrode 128 includes a plurality of electrical elements 502-522, which are effectively electrically insulated from one another and which are set to varying voltages (linear, exponential) across the width of the second plate electrode 128, from about −28 volts to about −11,000 volts. The plurality of electrical elements 502-522 extends along the length of the second plate electrode 128 and the electrical elements 502-522 are closely spaced along the width of the second plate electrode 128. The electrical elements 502-522 can be in a form of linear wires having a diameter, as well other linear shapes adapted to be disposed along the second plate electrode 128. More specifically, at least one electrical element 502 is configured to be set to a first voltage, such as about −28 volts, at the first portion 406 along the width of the second plate electrode 128. At least one electrical element 522 is configured to be set a second voltage, such as −11,000 volts, at the second portion 408 along the width of the second plate electrode 128. A plurality of electrical elements 504-520 are configured to be set to varying voltages at the central portion 403, such as between about −28 volts and about −11,000 volts, the voltage rising linearly or exponentially along the width 404 of the second plate electrode 128.

Figure 6:
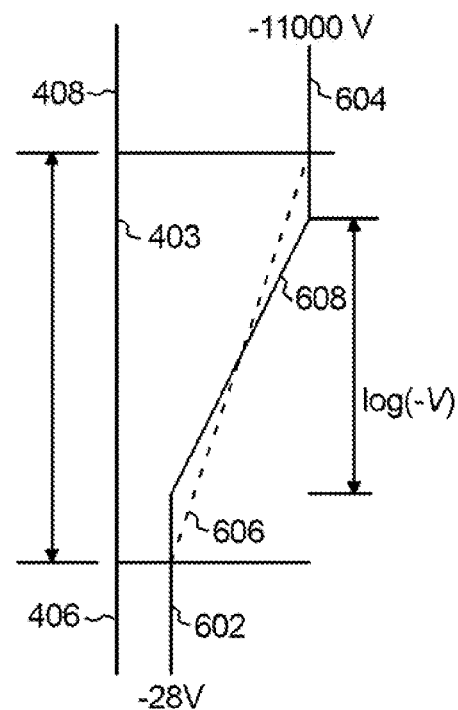
FIG. 6 illustrates linear and exponential voltages of the second plate electrode illustrated in FIGS. 4 and 5.

FIG. 6 illustrates linear and exponential voltages of the second plate electrode 128 illustrated in FIGS. 4 and 5. At the first section 406 of approximately 2.6 cm, the second plate electrode 128 is set to a first constant voltage 602 of about −28 volts. At the second section 408 of approximately 2.6 cm, the second plate electrode 128 is set to a second constant voltage 604 of about −11,000 volts. At the second section 408 of approximately 6 cm, the second plate electrode 128 is set to varying voltages between about −28 volts and about −11,000. In one embodiment, the voltages rise linearly from about −28 volts to about −11,000 volts. In another embodiment, the voltages rise exponentially from about −28 volts to about −11,000 volts. Although, the theoretical analysis of the WSR-FIMS system 100 that follows is based on an embodiment of exponentially varying voltage, an embodiment of the linear voltage change can be described as shown by the equation:

$$V(a, y) = \begin{cases} -V_1, & \text{at } -b/2 \le y \le -b_1/2 \\ -\dfrac{V_2 - V_1}{b_1} y - \dfrac{V_2 + V_1}{2} & \text{at } -b_1/2 \le y \le b_1/2 \\ -V_2 & \text{at } b_1/2 \le y \le b/2 \end{cases}$$

The embodiment of the exponential voltage change can be described as shown in equation (1) below.

$$V(a, y) = \begin{cases} -V_1, & \text{at } -b/2 \le y \le -b_1/2 \\ -\sqrt{V_1 V_2} \exp(\mu y) & \text{at } -b_1/2 \le y \le b_1/2 \\ -V_2 & \text{at } b_1/2 \le y \le b/2 \end{cases} \quad (1)$$

$$\text{where } \mu = \dfrac{1}{b_1} \ln\!\left(\dfrac{V_2}{V_1}\right)$$

With the first plate electrode 122 grounded and the second plate electrode set to voltages described above in equation (1), the potential field inside the separation section 116 can be described as shown in equation (2) below.

$$V(x, y) = \sum_{n=1}^{+\infty} B_n \dfrac{\sinh\!\left(\dfrac{n\pi}{b_0} x\right)}{\sinh\!\left(\dfrac{n\pi a}{b_0}\right)} \sin\!\left(\dfrac{n\pi(y + 0.5 b_0)}{b_0}\right), \quad (2)$$

$$0 \le x \le a,$$

$$-b/2 \le y \le b/2$$

where $b_0 \gg b$, and $b_0 = 3b$ is used. The details of the derivation and the coefficients $B_n$, are shown by the equation:

$$B_n = -\dfrac{2V_1}{n\pi}\left[1 - \cos\!\left(\dfrac{n\pi(b_0 - b_1)}{2 b_0}\right)\right] -$$

$$\dfrac{2V_2}{n\pi}\left[\cos\!\left(\dfrac{n\pi(b_0 + b_1)}{2 b_0}\right) - (-1)^n\right] - \dfrac{2\sqrt{V_1 V_2}}{(\mu b_0)^2 + (n\pi)^2}$$

$$\left\{\exp\!\left(\dfrac{\mu b_1}{2}\right)\!\left[\mu b_0 \sin\!\left(\dfrac{n\pi(b_0 + b_1)}{2 b_0}\right) - n\pi \cos\!\left(\dfrac{n\pi(b_0 + b_1)}{2 b_0}\right)\right] -\right.$$

$$\left.\exp\!\left(-\dfrac{\mu b_1}{2}\right)\!\left[\mu b_0 \sin\!\left(\dfrac{n\pi(b_0 - b_1)}{2 b_0}\right) - n\pi \cos\!\left(\dfrac{n\pi(b_0 - b_1)}{2 b_0}\right)\right]\right\}$$

As the potential field is independent of z, the electrical field E has no z-dimension. The x- and y-dimensions of the electric field E obtained from equation (2) can be described as shown in equation (3) below:

$$E_x = -\dfrac{\partial V(x, y)}{\partial x} \quad (3)$$

$$E_y = -\dfrac{\partial V(x, y)}{\partial y}$$

The theoretical analysis of the WSR-FIMS system 100, including the transfer function, resolution, transmission efficiency of the WSR-FIMS system 100, as well as operational examples, are described below with reference to FIGS. 7 through 17.

Transfer Function

Nanometer particles as small as 10 nm can be grown inside the condenser 134 into sufficiently sized conglomerate particles for detection, and their positions and concentrations can be accurately derived from the one or more images obtained by the detector 182. As the WSR-FIMS system 100 involves the modification of the electric field inside the separator section 116, the following analysis focuses on particle trajectories inside the separator sections 116 and their positions at the exit of separator section 116. The trajectories are used to examine the performance of the WSR-FIMS system 100. For simplification, the flow inside the separator section 116 is assumed to be fully developed, and the analysis focuses on non-diffusing particles. It is expected that Brownian diffusion of particles should not affect the dynamic measurement size range of the WSR-FIMS system 100. The influence of particle diffusion on the size resolution of WSR-FIMS system 100 will be discussed in greater detail below. Inside the separator section 116, a fully developed flow in a center region can be described by the two-dimensional laminar flow as shown in equation (4) below:

$$u_z = \dfrac{6 Q_t}{a^3 b} x(a - x) \quad (4)$$

$$u_x = u_y = 0$$

where $Q_t$ is the total flow rate (e.g., sum of $Q_a$ and $Q_{th}$), and a, the gap between the two plate electrodes 122, 128 of the separator section 116. $Q_{th}$ is the flow rate of the first fluid stream 162 and $Q_a$ is the flow rate of the second fluid stream 164. The edge effect of flow near the plate electrodes 122, 128 of the separator section 134 (e.g., near y=b/2 or −b/2) is neglected, as only particles detected in the center region of the cross section are used to derive size distributions. Based on the flow field, the flow streamline function can be described as shown in equation (5) below:

$$\Psi = \int^{x,z}(u_z dx - u_x dz) = \int^x u_z dx \quad (5)$$

Equations (4) and (5) show that $\Psi$ is function only of x. Similarly, an electric flux function can be described as shown in equation (6) below:

$$\Phi = \int^{x,y}(E_x dy - E_y dx). \quad (6)$$

Inside the separator section 116, the velocity of a particle with electrical mobility of $Z_p$ can be described as shown in equation (7) below:

$$U = U_x i + U_y j + U_z k = Z_p E_x i + Z_p E_y j + u_z k \quad (7)$$

where $U_x$, $U_y$ and $U_z$ are x, y, and z components of the particle velocity, respectively. Combining equations (6) and (7), it can be shown that:

$$(U_x i + U_y j) \cdot \left(\frac{\partial \Phi}{\partial x} i + \frac{\partial \Phi}{\partial y} j\right) = (E_x Z_p i + E_y Z_p j) \cdot (-E_y i + E_x j) = 0 \quad (8)$$

Equation (8) indicates that inside the separator section 116, the projection of particle trajectory on the x-y plane corresponds to constant electric flux function as shown in equation (9) below:

$$\Phi(x, y) = \text{constant} \quad (9)$$

Figure 7:
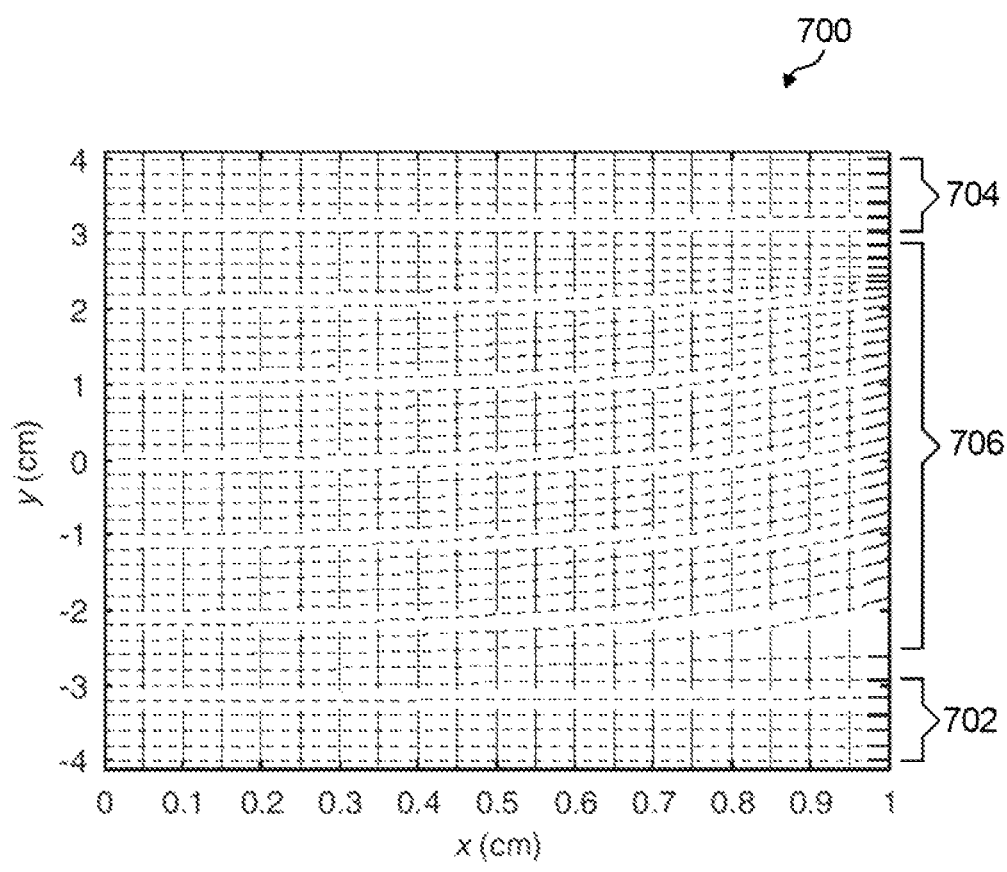
FIG. 7 illustrates a graph showing lines that correspond to constant flow streamline and constant electric flux.

FIG. 7 illustrates lines that correspond to constant flow streamline (vertical) and constant electric flux (horizontal). As $\Psi$ is a function of x only, a constant flow streamline corresponds to a constant x-coordinate, and is parallel to the y-axis. In contrast, electric flux $\Phi$ depends on both the x- and y-coordinates. It is worth noting that near the grounded first plate electrode 122 (e.g., x=0) the y-component of the electric field is small and constant electric flux lines are generally parallel to the x-axis. In the remainder of analysis, certain derivations will occasionally switch between the x-y coordinates and the $\Psi$-$\Phi$ coordinates.

Let $\Psi_{1,in}$ and $\Psi_{2,in}$ denote the limiting flow streamlines that bound the flow of the second fluid stream 164. That is, particles can be introduced along any flow streamlines that are between $\Psi_{1,in}$ and $\Psi_{2,in}$. In addition, particles can enter the separator along a range of $\Phi$ (e.g., at different y-locations at the second inlet 24). As the WSR-FIMS system 100 determines a particle's mobility from its position at the exit of the separator section 116, the instrument response mobility $Z^*_p$ is defined as follows to facilitate the analysis. For a non-diffusing particle that enters the separator section 116 along the central inlet flow streamline, $$\Psi_{c,in} = \frac{\Psi_{1,in} + \Psi_{2,in}}{2},$$

the instrument response mobility, $Z^*_p$, at the location where the particle exits the separator section 116 will be the same as the particle mobility $Z_p$. The instrument response mobility $Z^*_p$ defined in this application is a function of both the x- and y-coordinates at the exit of the separator section 116 due to the non-uniform electric field employed.

Next a particle with mobility $Z_p$ that is introduced into the separator section 116, along flow streamline $\Psi_{in}$ electric flux line $\Phi$, is considered. As the projection of the particle trajectory on the x-y plane corresponds to a constant electric flux function, the particle remains on the same electric flux line $\Phi$, at the exit of the separator section 116. The probability of a particle with mobility $Z_p$ introduced into the separator section 116 and measured by the WSR-FIMS system 100 with instrument response mobility from $Z^*_p$ to $Z^*_p + dZ^*_p$ can be described as shown in equation (10) below:

$$P(Z_p, Z^*_p) dZ^*_p = \left[\int_{\Phi_{min}}^{\Phi_{max}} \int_{\Psi_{1,in}}^{\Psi_{2,in}} f_{t-nd}(Z_p, \Psi_{in}, \Phi, Z^*_p) f_e(\Psi_{in}, \Phi) d\Psi_{in} d\Phi\right] dZ^*_p \quad (10)$$

where $f_e(\Psi_{in}, \Phi) d\Psi_{in} d\Phi$ is the probability that a particle is introduced between flow streamline $\Psi_{in}$ and $\Psi_{in} + d\Psi_{in}$ and between electric flux line $\Phi$ and $\Phi + d\Phi$. The quantity $f_e(\Psi_{in}, \Phi)$ can be derived as follows. First, switch coordinate to $\Phi$ to y and define $f'_e(\Psi_{in}, y_{in})$ as the probability density that particles enter the separator section 116 along flow streamline $\Psi_{in}$ at position $y_{in}$. Based on its definition, $f'_e(\Psi_{in}, \Phi)$ can be described as shown in equation (11) below:

$$f'_e(\Psi_{in}, y_{in}) = \frac{1}{\Psi_{2,in} - \Psi_{1,in}} \cdot \frac{1}{b} \quad (11)$$

From the definitions of $f_e(\Psi_{in}, \Phi)$ and $f'_e(\Psi_{in}, y_{in})$, it follows that, as shown in equation (12) below:

$$f_e(\Psi_{in}, \Phi) d\Psi_{in} d\Phi = f'_e(\Psi_{in}, y_{in}) d\Psi_{in} dy_{in}, \quad (12)$$

and therefore, $$f_e(\Psi_{in}, \Phi) = f'_e(\Psi_{in}, y_{in}) \left(\frac{d\Phi}{dy_{in}}\right)^{-1} \quad (13)$$

$$= \frac{1}{(\Psi_{2,in} - \Psi_{1,in}) \cdot b \cdot E_x(\Psi_{in}, \Phi)}$$

The quantity $f_{t-nd}(Z_p, \Psi_{in}, \Phi, Z^*_p)$ is the probability of a non-diffusing particle with mobility $Z_p$, introduced at $\Psi_{in}$ and $\Phi$, measured with an instrument response mobility between $Z^*_p$ and $Z^*_p + dZ^*_p$, and can be described as shown in equation (14) below:

$$f_{t-nd}(Z_p, \Psi_{in}, \Phi, Z^*_p) dZ^*_p = \delta[Z^*_p - Z^*_{p,out}(Z_p, \Psi_{in}, \Phi)], \quad (14)$$

where $Z^*_{p,out}(Z_p, \Psi_{in}, \Phi)$ is the instrument response mobility for a particle with mobility $Z_p$, and introduced into separator section 116 at $\Psi_{in}$ and $\Phi$. In this analysis, the probability density function $P(Z_p, Z^*_p)$ is also referred to as the transfer function of the WSR-FIMS system 100.

To facilitate this analysis, a sub-probability density function is presented (i.e., sub-transfer function) for particles introduced at electric flux $\Phi$, $P(Z_p, \Phi, Z^*_p)$, which can be described as shown in equation (15) below:

$$P(Z_p, \Phi, Z^*_p) = \int_{\Psi_{1,in}}^{\Psi_{2,in}} f_{t-nd}(Z_p, \Psi_{in}, \Phi, Z^*_p) f_e(\Psi_{in}, \Phi) d\Psi_{in} \quad (15)$$

Combining equations (13), (14) and (15) yields equation (16) below:

$$P(Z_p, \Phi, Z^*_p) = \int_{\Psi_{1,in}}^{\Psi_{2,in}} \delta[Z^*_p - Z^*_{p,out}(Z_p, \Psi_{in}, \Phi)] \cdot \quad (16)$$

$$\frac{1}{(\Psi_{2,in} - \Psi_{1,in}) \cdot b \cdot E_x(\Psi_{in}, \Phi)} \cdot d\Psi_{in} =$$

$$\begin{cases} \frac{1}{(\Psi_{2,in} - \Psi_{1,in}) \cdot b \cdot E_x(\Psi^*_{in}, \Phi)} \left[\frac{\partial Z^*_{p,out}(Z_p, \Psi_{in}, \Phi)}{\partial \Psi_{in}}\bigg|_{\Psi^*_{in}}\right]^{-1}, \\ \text{when } \Psi_{1,in} \leq \Psi^*_{in} \leq \Psi \text{ and } Z^*_{p,out}(Z_p, \Psi^*_{in}, \Phi) \\ 0, \\ \text{otherwise} \end{cases}$$

As discussed below, only particles detected within a defined viewing area are used to derive size distribution. As a result, calculation of $P(Z_p, \Phi, Z^*_p)$ and therefore $P(Z_p, Z^*_p)$ also takes into account the restriction by the viewing area. That is, for $Z^*_p$ corresponding to a position that is outside the viewing area, $P(Z_p, \Phi, Z^*_p)$ is zero regardless of the value derived from equation (16) set forth above. From equations (10) and (15), the probability density function is given by the integral of the sub-probability density function over the range of $\Phi$ as shown in equation (17) below:

$$P(Z_p, Z^*_p) = \int^{\Phi_{max}} P(Z_p, \Phi, Z^*_p) d\Phi \qquad (17)$$

Switching from $\Phi$ to y coordinate at x=0 (e.g., $\Psi_{in}=0$), equation (17) can be rewritten as shown in equation (18) below:

$$P(Z_p, Z^*_p) = \int_{-b/2}^{b/2} E_x(0, y) P(Z_p, \Phi(y), Z^*_p) dy, \qquad (18)$$

Equation (18) can be approximated with a summation, as shown in equation (19) below:

$$P(Z_p, Z^*_p) = \frac{b}{n} \sum_{i=1}^{n} E_x(0, y_i) P(Z_p, \Phi(y_i), Z^*_p) \qquad (19)$$

As discussed in greater detail below, equation (19) above allows convenient derivation of $P(Z_p, Z^*_p)$ from $P(Z_p, \Phi, Z^*_p)$ simulated at $y_i$ evenly on the y-axis.

Mobility Resolution and Transfer Efficiency

In addition to measurement speed and dynamic size range, other important characteristics of mobility-based size instruments include the resolution and transmission efficiency. In a SMPS system, the instrument mobility resolution is traditionally described by $R_{FWHM}$, defined as the ratio of central mobility to the full width at half maximum (FWHM) of the mobility transfer function (e.g., probability density function). For non-diffusing particles, the $R_{FWHM}$ of the SMPS system is simply the ratio of sheath flow to aerosol flow rate. As shown later, $R_{FWHM}$ sometimes fails to capture the overall spread of the WSR-FIMS system 100 transfer function due to its unique shape. Therefore a new resolution $R_{std}$ based on standard deviation of the transfer function can be described as shown in equation (20) below:

$$R_{std}(Z_p) = \frac{Z_p}{\sigma_{Z^*_p}} = \frac{Z_p \cdot \int_0^{+\infty} P(Z_p, Z^*_p) dZ^*_p}{\int_0^{+\infty} (Z^*_p - \overline{Z^*_p})^2 P(Z_p, Z^*_p) dZ^*_p}, \qquad (20)$$

where $$\overline{Z^*_p} = \frac{\int_0^{+\infty} Z^*_p P(Z_p, Z^*_p) dZ^*_p}{\int_0^{+\infty} P(Z_p, Z^*_p) dZ^*_p}$$

Similarly, for a particle with mobility $Z_p$ introduced at electric flux line $\Phi$, the sub-resolution $R_{FWHM}$ can be similarly described as the ratio of the particle mobility to the FWHM of the sub-transfer function $P(Z_p, \Phi, Z^*_p)$, and sub-resolution $R_{std}(Z_p, \Phi)$ can be described by replacing $P(Z_p, Z^*_p)$ with $P(Z_p, \Phi, Z^*_p)$ in equation (20) described above.

The probability that an introduced particle be detected within defined viewing area at the exit of separator section 116 is described by the transmission efficiency $\eta(Z_p)$, which can be described as shown in the equation (21) below:

$$\eta(Z_p) = \int_0^{+\infty} P(Z_p, Z^*_p) dZ^*_p \qquad (21)$$

It should be noted that $P(Z_p, Z^*_p)$ takes into consideration the restriction of the viewing area; e.g., particles that exit outside the viewing area do not contribute to the $P(Z_p, Z^*_p)$ or to $\eta(Z_p)$.

EXAMPLES

Numerical Simulations and Cases

The performance of the WSR-FIMS system 100, as characterized by its wide measurement size range, resolution, and transmission efficiency, is calculated from the probability density function, which is derived from numerically simulated particle trajectories inside the separator section 116. In the FIMS system, it is established that the particle position in the x-y plane remains the same inside the condenser. In addition, particles as small as 10 nm in diameter are grown into super-micrometer droplets and efficiently detected by the CCD camera. Therefore, the particle position in the x-y plane at the exit of the separator section 116, which is expected to be the same as that captured by the image, is used to analyze the performance of the WSR-FIMS 100 in this analysis. The simulation of particle trajectory was carried out for particles of 4800 diameters evenly spaced on a logarithmic scale from 8 nm to 1800 nm. Particles of each size were introduced into the separator at 1001 locations $y_{in}$ that were evenly spaced from y=−4.0 to y=4.0 cm.

As discussed below, only particles detected within the central 6 cm (e.g., −3.0≤y≤3.0 cm) of the conduit 118 at the exit of the separator section 116 are used to derive size distributions. Particles introduced at position $y_{in}$<−4 cm or $y_{in}$>4 cm exit outside of the viewing area and their trajectories were not simulated. At each position $y_{in}$, particles were introduced along 101 flow streamlines that are evenly spaced between and that bound the flow. These resulted in simulation of 4800×1001×101=4.85×10$^8$ trajectories. The velocity and trajectory of each particle inside the separator section 116 were calculated from the particle electrical mobility, the electric field, and the flow field using equations (2), (3), (4), and (7) described hereinabove.

The particle positions (e.g., x- and y-coordinates) at the exit of the separator section 116 were then derived from the simulated trajectories. Based on its definition, the instrument response mobility $Z^*_p$ was mapped using the exit positions of particles introduced along the central flow streamline $\Psi_{c,in}$ and their electrical mobilities. The instrument response mobilities for particles introduced along other inlet flow streamlines, which allow the derivation of transfer function using equations (16) and (19), were then computed using their exit positions and the mapped $Z^*_p$. Simulations were also carried by doubling the number of particle diameters, the number of $y_{in}$ positions, or the number of flow streamlines along which particles were introduced into the separator section 116, and no appreciable difference was found in the simulated transfer function, resolution, or transmission efficiency.

The simulations were carried out for two representative operating configurations, both of which have the same physical dimensions of the separator section and the same voltage applied to the HV electrode (Table 1). Immediately below, Table 1 illustrates approximate physical dimension and operation parameters for simulated configurations 1 and 2.

TABLE 1

| Dimension or Operation condition | Configuration 1 | Configuration 2 |
|---|---|---|
| Distance between separator electrodes, a | 1 cm | 1 cm |
| Width of channel, b | 10 cm | 10 cm |
| Length of separator, $l_s$ | 25 cm | 25 cm |
| Minimum Voltage, $V_1$ | 27.9 V | 27.9 V |
| Maximum Voltage, $V_2$ | 11250 V | 11250 V |
| $b_1$ | 4.8 cm | 4.8 cm |
| $\mu$ | 1.25 cm$^{-1}$ | 1.25 cm$^{-1}$ |
| Sheath flow rate, $Q_{sh}$ | 10 L min$^{-1}$ | 10 L min$^{-1}$ |
| Aerosol flow rate, $Q_a$ | 0.2 L min$^{-1}$ | 1 L min$^{-1}$ |
| Range in x axis of the viewing area | 0.2-0.87 cm | 0.5-0.87 cm |
| Range in y axis of the viewing area | −3.0-3.0 cm | −3.0-3.0 cm |

The differences between the two configurations are the aerosol sample flow rate $Q_a$ and the corresponding viewing area. In the first configuration, $Q_a$ is 0.2 L min$^{-1}$, corresponding to a $Q_{sh}/Q_a$ ratio of 50. In the second configuration, $Q_a$ is increased to 1 L min$^{-1}$, corresponding to $Q_{sh}/Q_a$ of 10.

Particle Trajectory, Resolution and Transmission Efficiency

Figure 9:
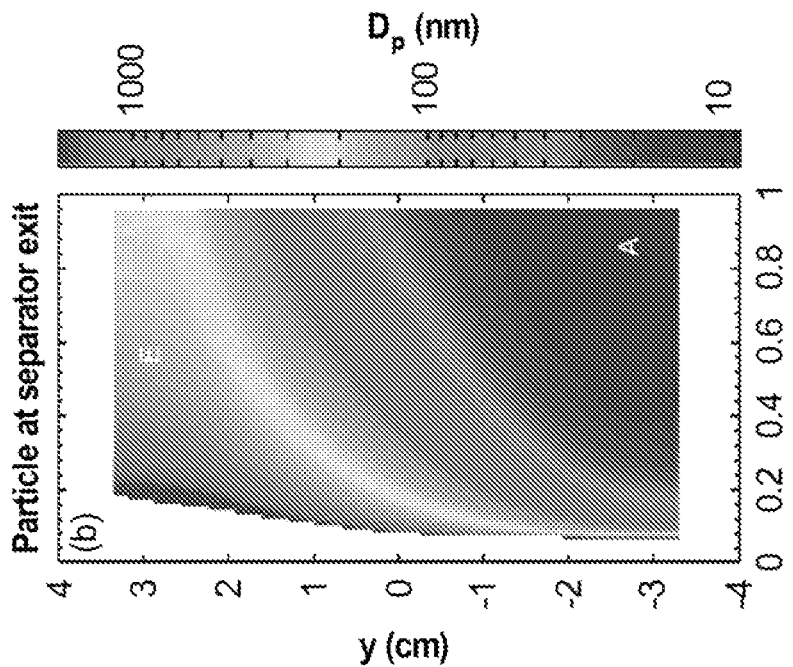
FIG. 9 illustrates a graph showing positions of particles at the exit of the separator section of the WSR-FIMS system illustrated in FIG. 1.
Figure 8:
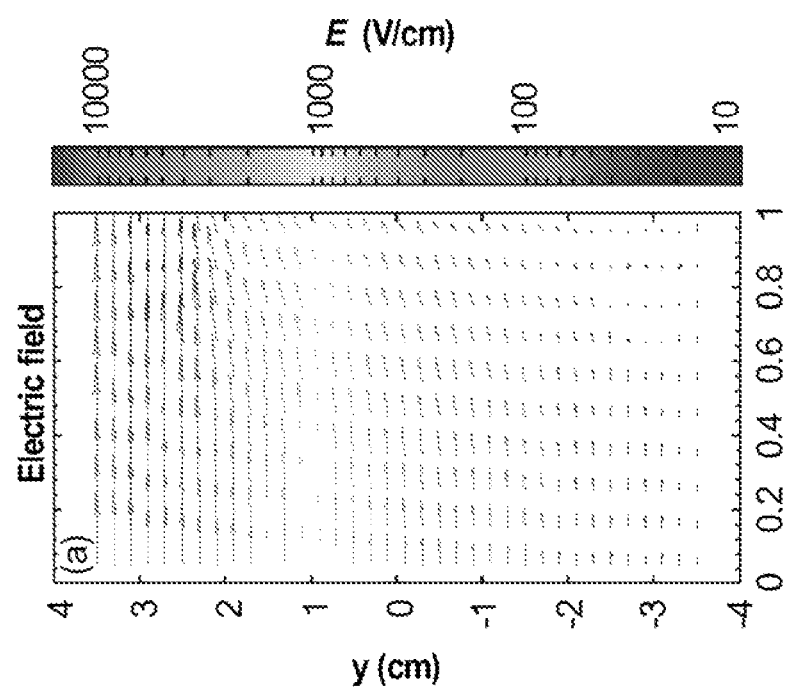
FIG. 8 illustrates a graph showing the calculated electric field inside the separator section of the WSR-FIMS system illustrated in FIG. 1.

FIG. 8 illustrates a graph showing the calculated electric field inside the separator section 116 of the WSR-FIMS system 100. FIG. 9 illustrates positions at the exit of the separator section 116 of particles ranging from 10 to 1600 nm, introduced along the central inlet flow streamlines under configuration 1, particle positions being color-coded in accordance with particle diameter. Because the particle exit positions for configuration 2 are very similar, they are not shown herein. As further shown in FIG. 8, the electric field strength varies over three orders of magnitude. Due to the constant voltage applied at both ends of the HV electrode (e.g., y<−2.4 cm or y>2.4 cm), the electric field near both ends is essentially uniform and has no appreciable y-component (e.g., it is perpendicular to the HV electrode). In contrast, the electric field in the center of the separator section 116 cross section (shown in FIG. 4) has a large y-component as a result of the variation in applied voltage. As expected, particles with large diameters (e.g., low electrical mobilities) exit the separator section 116 at regions with strong electric field, whereas small particles are separated spatially in regions with weak electric field. It should be noted that in regions with strong electric field particles with small diameters move very fast such that they deposit on the separator wall before exiting the separator section 116. As a result, particles with small diameters cannot be measured in the regions with strong electric field. In the WSR-FIMS system 100, particles introduced at different $y_{in}$ experience different electric field strengths of the non-uniform electric field, and particles of same size may exit at a range of x-coordinates, creating arcuate bands in the direction of the electric field, as shown in FIG. 9.

Figure 10:
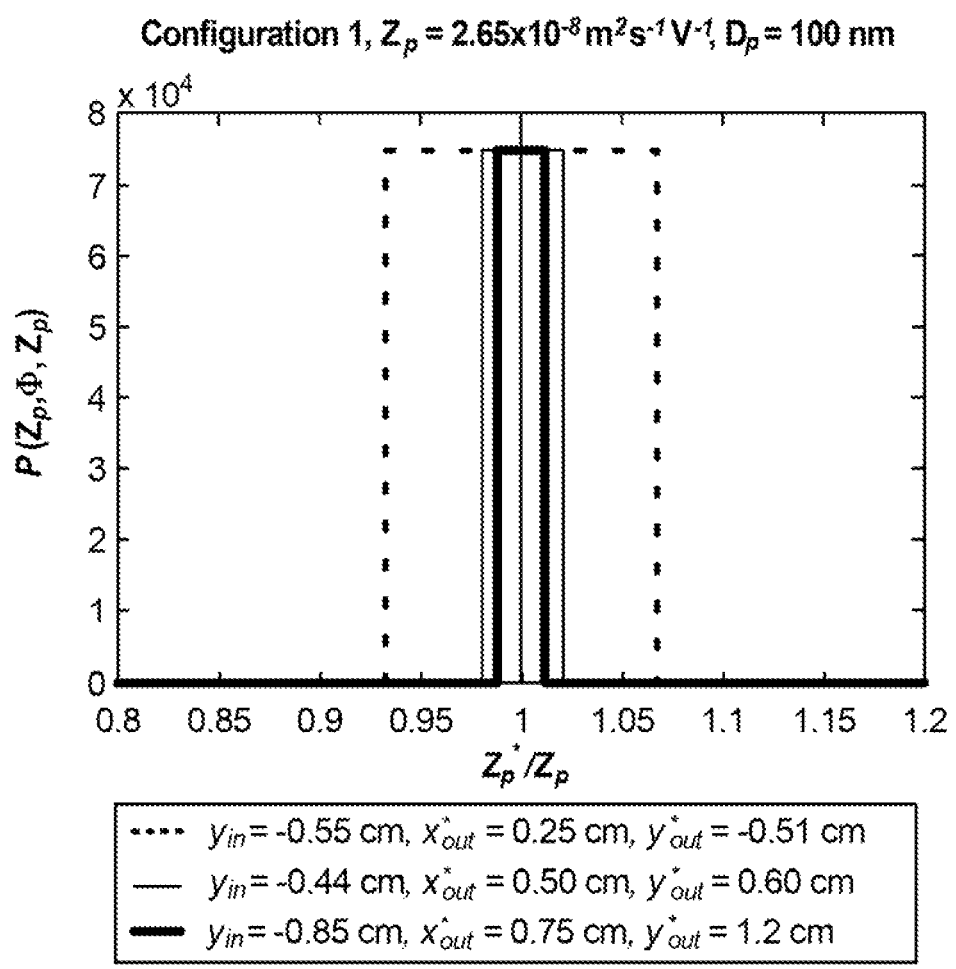
FIG. 10 illustrates a graph of the sub-transfer function for 100 nm particles introduced into the separator section of the WSR-FIMS system of FIG. 1 in a first configuration.

FIG. 10 illustrates the sub-transfer function $P(Z_p, \Phi, Z^*_p)$ for 100 nm particles introduced at different $y_{in}$ locations (e.g., along different electric flux line $\Phi$) under configuration 1. The electrical mobility is calculated from particle diameter ($D_p$) at a temperature of 25° C. and a pressure of 1013 hPa, assuming singly charged particles. As shown in FIG. 10, the sub-transfer function is a rectangle for non-diffusing particles. Particles introduced with greater $y_{in}$ experience a stronger electric field, exiting the separator section 116 with greater x-coordinates, and thus have a narrower transfer function as shown in FIG. 10. As an example, if x*$_{out}$ and y*$_{out}$ denote the coordinates at the exit of the separator section 116 for particles introduced along the central inlet flow streamline $\Psi_{c,in}$, for 100 nm particles introduced at $y_{in}$ of −0.55, 0.44, and 0.85 cm, the corresponding x*$_{out}$ is 0.25, 0.5 and 0.75 cm and y*$_{out}$ is −0.51, 0.62, and 1.2 cm, respectively.

Figure 11:
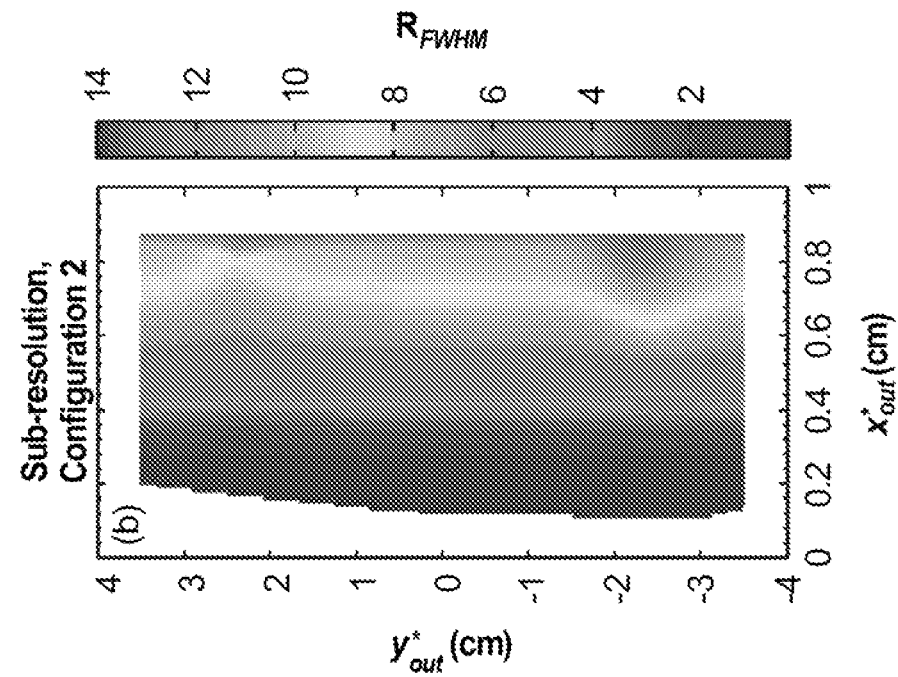
FIG. 11 illustrates a graph of sub-resolution as a function of locations of the particles at the exit of the separator section of the WSR-FIMS system of FIG. 1 in the first configuration.
Figure 12:
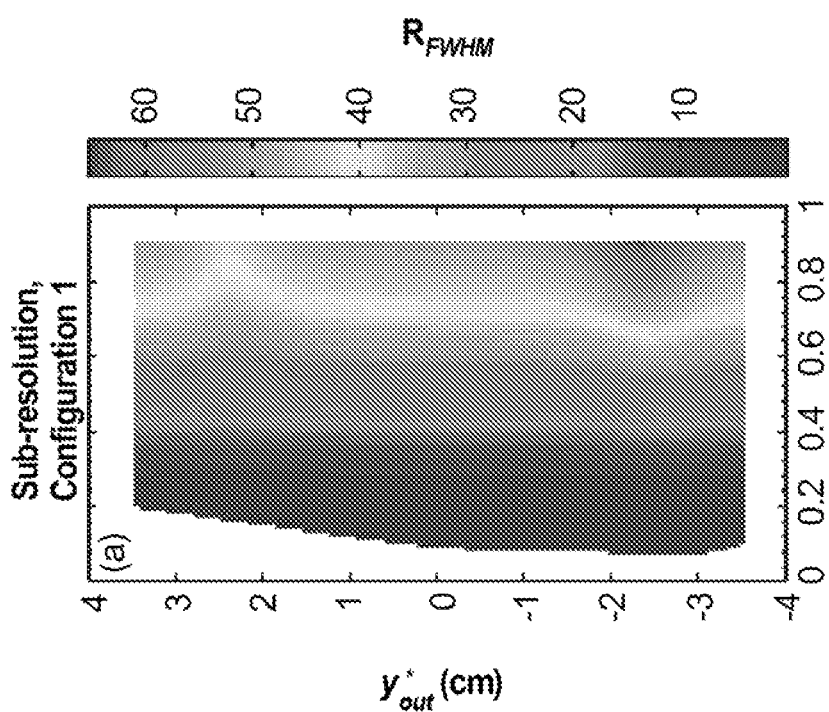
FIG. 12 illustrates a graph of sub-resolution as a function of locations of the particles at the exit of the separator section of the WSR-FIMS system of FIG. 1 in a second configuration.

FIG. 11 illustrates the sub-resolution $R_{FWHM}$ as a function of x*$_{out}$ and y*$_{out}$ at the exit of the separator section 116 for the WSR-FIMS system 100 in configuration 1. FIG. 12 illustrates the sub-resolution $R_{FWHM}$ as a function of x*$_{out}$ and y*$_{out}$ at the exit of the separator section 116 for the WSR-FIMS system 100 in configuration 2. The sub-resolution $R_{FWHM}$ in WSR-FIMS system 100 is mainly determined by x*$_{out}$ and has a weak dependence on y*$_{out}$. The dependence on y*$_{out}$ is found mostly near the second plate electrode 128 at y*$_{out}$ equal to 2.4 and −2.4 cm, which correspond to the start and the end of the region where negative voltage source 130 applied to second plate electrode 128 varies exponentially. For both configurations 1 and 2, the sub-resolution $R_{FWHM}$ generally increases with increasing x*$_{out}$, reaching its maximum of approximately $Q_{sh}/Q_a$ at the second plate electrode 128. Configuration 1 has higher $R_{FWHM}$ than configuration 2 due to its much higher ratio of $Q_{sh}/Q_a$. To achieve a good overall resolution, the viewing area (e.g., area within which detected particles are used to derive size distribution) is defined as 0.20≤x*$_{out}$≤0.87 cm and −3≤x*$_{out}$≤3 cm for configuration 1. For configuration 2, due to its lower sub-resolution, the viewing area is reduced to 0.5≤x*$_{out}$≤0.87 cm and −3≤x*$_{out}$≤3 cm to maintain a sufficient overall resolution.

Figure 14:
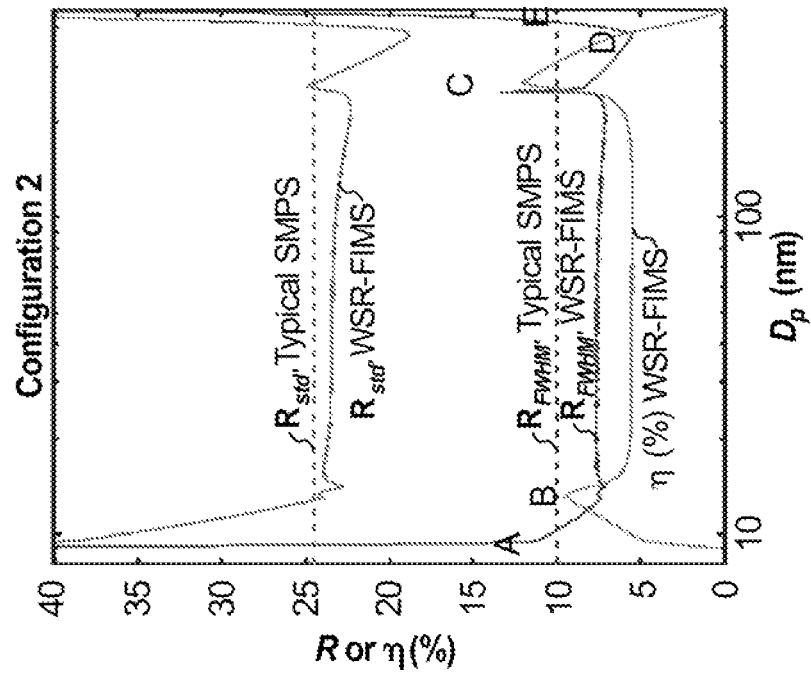
FIG. 14 illustrates a graph of transmission efficiency and resolution of the WSR-FIMS system of FIG. 1 in the second configuration.
Figure 13:
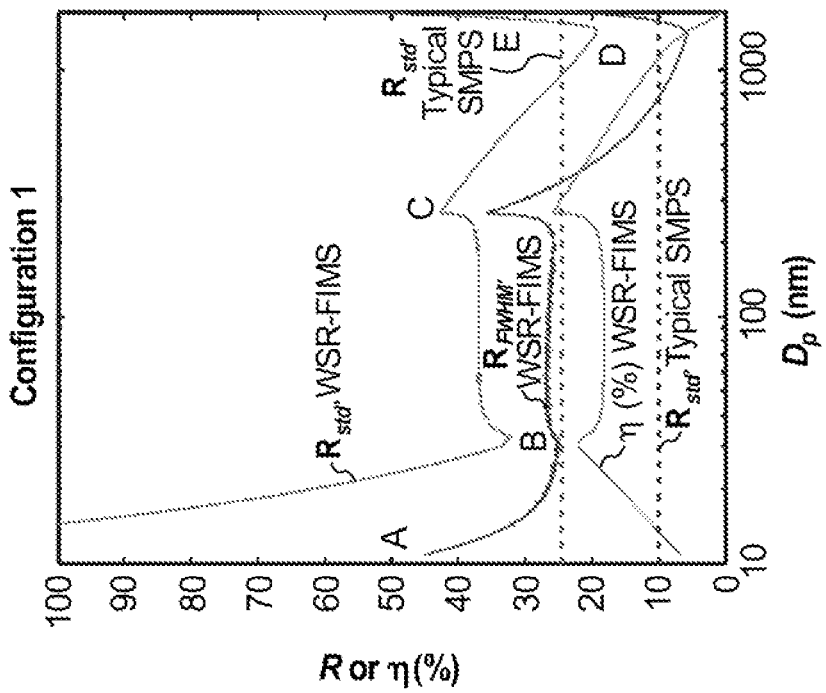
FIG. 13 illustrates a graph of transmission efficiency and resolution of the WSR-FIMS system of FIG. 1 in the first configuration.

FIG. 13 illustrates transmission efficiency and the resolution for the WSR-FIMS system 100 for configuration 1. FIG. 14 illustrates transmission efficiency and the resolution for the WSR-FIMS system 100 for configurations 2. $R_{FWHM}$, $R_{std}$ and $\eta$ of the two configurations show similar variations over the measurement size range. Near the lower limit of measurement range, $\eta$ first increases with increasing $D_p$, reaches its first peak at point B, then decreases and stays relatively constant over a large fraction of the measurement size range. The transmission efficiency then increases again to reach its second peak at point C before decreasing as $D_p$ further increases to the upper limit of measurement range. Both $R_{FWHM}$ and $R_{std}$ start with high values at the lower end of measurement size range. As $D_p$ increases, both resolutions first reach a local minimum (Point B), then remain nearly constant over a large size range. As $D_p$ further increases, the resolutions reach a local maximum at point C, then decrease before rising again near the upper limit of the measurement size range.

For configuration 1, $\eta$ is greater than 18% (e.g., more than 18% of the charged particle introduced are detected within the viewing area) for $D_p$ ranging from 23 nm to 550 nm, with lower transmission efficiency outside this range, decreasing to 10% at 14 nm and 1120 nm, and 5% at 10 and 1470 nm. For configuration 2, $\eta$ is greater than 5.5% for $D_p$ ranging from 9.9 nm to 385 nm, decreasing to less than 3% for particles larger than 408 nm or smaller than 9.3 nm in diameter. Over most of the measurement range, both $R_{std}$ and $R_{FWHM}$ of configuration 1 are greater than those of the SMPS system (e.g., operated at $Q_{sh}/Q_a$ of 10), which are 24.5 and 10, respectively. For configuration 2, $R_{std}$ is lower than that of configuration 1, but is still about the same as that of SMPS system except for large particles with $D_p$ greater than about 300 nm. It is expected that the slightly lower resolution at large $D_p$ will not affect the measurements of ambient aerosols, which often show broad distributions in this size range. Compared to configuration 1, configuration 2 has a relatively narrower measurement size range because large particles do not travel far enough into the reduced viewing area. However, even configuration 2 provides a much increased dynamic size range (e.g., 10 to 400 nm) compared to the FIMS system that has a typical mobility range of a factor of 10, corresponding to a size range between a factor of 3.5 and 5.5 for sub-micrometer particles. It is worth noting that $Q_a$ in configuration 2 is 5 times of that in configuration 1. As a result, despite its lower η, configuration 2 has an overall higher sampling rate than configuration 1 at the expense of a narrower measurement size range.

The remainder of this section explains the variations of $R_{std}$, $R_{FWHM}$, and η illustrated in FIGS. 13 and 14. As the two configurations exhibit similar features in their variations, the discussion will focus on configuration 2. The variation in η will be discussed first, followed by the variation of both $R_{std}$ and $R_{FWHM}$ near the upper measurement size range (Points C, D, and E shown in FIG. 14), and finally the variations in resolutions near the lower limit of the measurement range (Points A and B in FIG. 14).

As the strength of the electric field varies significantly with respect to the y-coordinate, at a $D_p$, only particles introduced within a certain range of $y_{in}$ are detected within the defined viewing area at the exit of the separator section 116. Because particles do not move in the x- and y-coordinates in the condenser section 134 as there is no electric field, the defined viewing area is the same as at the exit of the condenser section 134. This range is referred as the "effective" $y_{in}$ range for the given $D_p$. Particles introduced at $y_{in}$ above its effective range experience too strong an electric field such that particles either hit the second plate electrode 128 or exit the separator section 116 with an x-coordinate beyond the upper limit of the viewing area (x≤0.87 cm). At the same time, particles introduced with $y_{in}$ below the effect range experience an electric field that is too weak to move the particles into the viewing area. To a first order, η at a given $D_p$ is proportional to the corresponding effective $y_{in}$ range. The peaks of η at points B and C, corresponding to $D_p$ of 13 nm and 265 nm for configuration 2, are due to the constant voltages applied to both ends of the second plate electrode 128; e.g., 27.9 V at y≤−2.4 cm, and 11,250 V at y≥2.4 cm, which result in nearly uniform electric fields in these two regions, as shown in FIG. 8. The two regions 406, 408 are referred to as the "uniform weak electric field" and "uniform strong electric field" regions, respectively, and the region of −2.4≤y≤2.4 cm is referred to as the center region with exponentially varying electric field. At $D_p$ of 265 nm, the effective $y_{in}$ range is 1.64≤y≤2.98 cm ($\Delta y_{in}$=1.34 cm), which includes nearly the entire region of uniform strong electric field within the viewing area (2.4≤$y_{in}$≤2.98 cm).

In contrast, particles ranging from 20 nm to 220 nm are detected mostly within the region with the exponentially varying electric field, and therefore the corresponding effective $y_{in}$ range is substantially narrower. For example, the effective $y_{in}$ range for 150 nm particle is 0.9 to 1.58 cm ($\Delta y_{in}$=0.68 cm), about 50% of the effective range at 265 nm. As a result, for particles detected mainly within the center region of the separator section 116 with varying electric field, η is lower and relatively constant. As $D_p$ further increases from 265 nm and approaches the upper limit of the size measurement range, the effective $y_{in}$ range and η also decrease because for particles near the upper limit of measurement range, only those introduced at the region with the strongest electric field are detected within the viewing area. For example, at diameter of 400 nm, the effective yin range is reduced to 2.3≤$y_{in}$≤3 cm. The above variations in effective $y_{in}$ range lead to a peak in η at 265 nm (Point C in FIG. 14). Similarly, the peak in η at 13 nm corresponds to an effective $y_{in}$ range from −3 cm to −2.04 cm. The effective $y_{in}$ range at 13 nm includes the entire section with the weakest and constant electric field (−3≤$y_{in}$≤−2.4 cm) in addition to a section within the region with spatially varying electric field (e.g., −2.4≤$y_{in}$≤−2.04 cm). As $D_p$ decreases from 13 nm and approaches the lower limit of measurement range, the effective $y_{in}$ range decreases because only particles introduced within the region with the weakest electric field can exit the separator section 116 within the viewing area. For example, the effective $y_{in}$ range of 10 nm particles is limited to −3≤$y_{in}$≤−2.45 cm.

The sub-resolution for a given particle size mainly depends on the particle $x^*_{out}$ as shown in FIGS. 11 and 12. Particles introduced at high $y_{in}$ within the effective range are associated with high $x^*_{out}$, corresponding to high sub-resolution and a narrow sub-transfer function. The overall resolution can be viewed as the average of the sub-resolutions corresponding to particles introduced over the effective $y_{in}$ range. For configuration 2, $R_{std}$ also reaches a peak near 265 nm (Point C in FIG. 14). As discussed above, the effective $y_{in}$ range at 265 nm includes nearly the entire region of the uniform strong electric field within the viewing area (2.4≤$y_{in}$≤2.98 cm) in addition to a section within the region of exponentially varying electric field (e.g., 1.64≤$y_{in}$≤2.4 cm). Particles with diameter of 265 nm that are introduced within the region of uniform strong electric field have high $x^*_{out}$ (e.g., near the upper limit of the viewing area, 0.871 cm), which corresponds to high sub-resolution. Due to the large contribution of these particles with high $x^*_{out}$ the overall resolution at 265 nm is higher than those of smaller particles with effective $y_{in}$ range within the center region where the electric field varies exponentially. As $D_p$ further increases from 265 nm, the $x^*_{out}$ for particles introduced within the uniform strong electric field region decreases, resulting in a decrease of the overall $R_{std}$ from 265 nm to 380 nm (Points C to D in FIG. 14). The above variation in $R_{std}$ leads to a peak value of 25 at 265 nm. It is noted that $R_{FWHM}$ shows a much sharper peak than $R_{std}$ near point C, especially for configuration 2, where the peak occurs at 250 nm, slight less than the peak diameter of $R_{std}$ at 265 nm. The insight into the sharp peak of $R_{FWHM}$ can be gained by examining the sub-transfer function $P(Z_p, \Phi, Z^*_p)$ of particles with 250 um diameter (e.g., $Z_p$=6.24×10$^{-9}$ m$^2$s$^{-1}$V$^{-1}$) for configuration 2. Whereas typical $P(Z_p, \Phi, Z^*_p)$ has a rectangular shape and is symmetric around $Z_p$, this symmetry may cease to exist when measurements are restricted by the defined viewing area at the exit of separator section 116. Note that particles are introduced into the separator section 116 along different flow streamlines ranging from $\Psi_{1,in}$ to $\Psi_{2,in}$.

Figure 15:
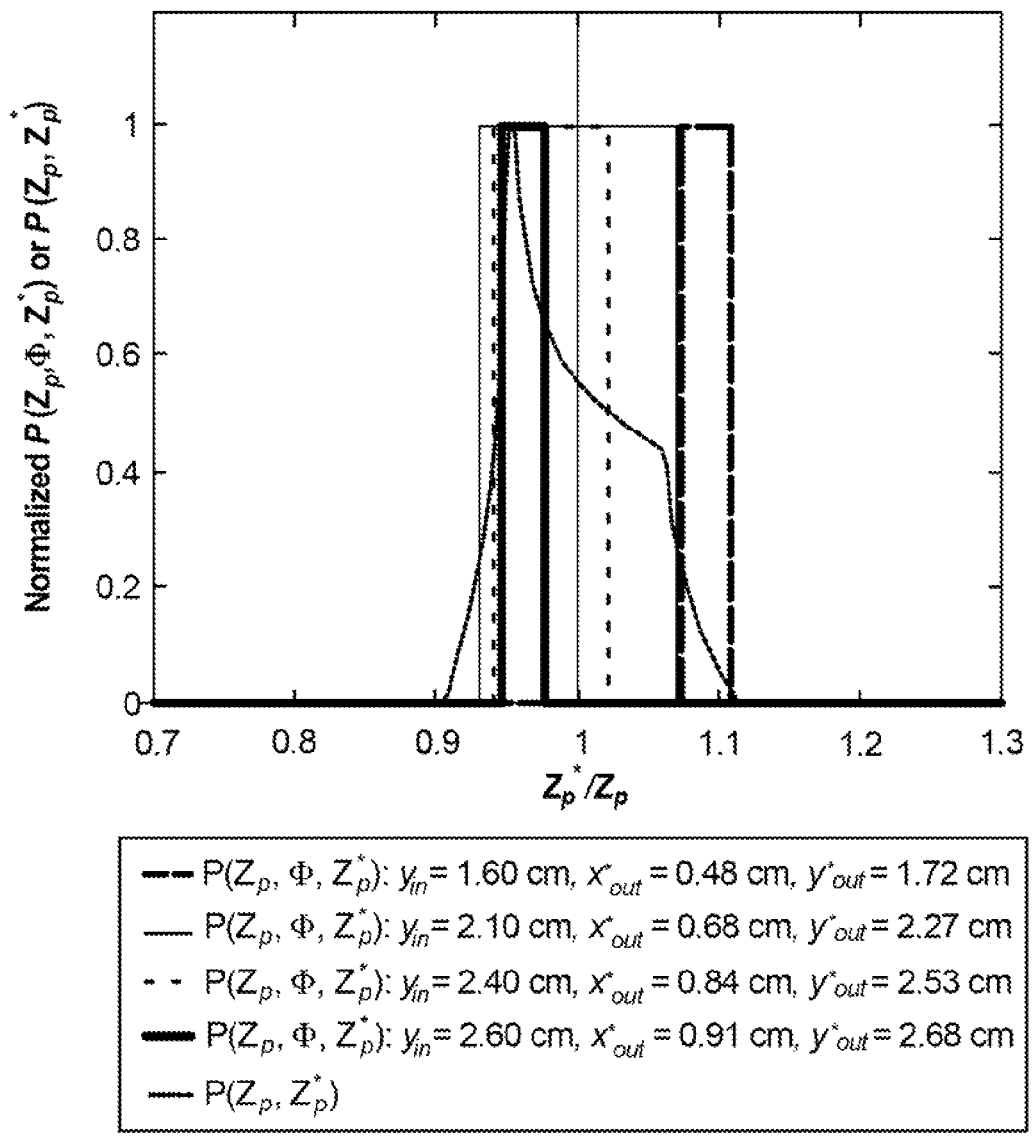
FIG. 15 illustrates a graph of normalized sub-transfer function and an overall transfer function for 250 nm particles in the second configuration.

FIG. 15 illustrates normalized sub-transfer functions and an overall transfer function for 250 nm particles under configuration 2. For example, at $y_{in}$=2.6 cm, particles with diameter of 250 nm introduced along the central inlet flow streamline $\Psi_{c,in}$ exit the separator section 116 outside of the viewing area (x>0.871 cm). As a result, at $y_{in}$=2.6 cm, only 250 nm particles introduced at some flow streamlines $\Psi<\Psi_{c,in}$ are detected within the viewing area and contribute to the sub-transfer function. This leads to an asymmetric sub-transfer function that is non-zero only at $Z^*_p<Z_p$ as shown in FIG. 15. At $y_{in}$=2.4 cm, whereas 250 nm particles introduced along are detected within the viewing area, particles introduced at the upper limit of the inlet flow streamline $\Psi_{2,in}$, in still exit out of the viewing area. As a result, $P(Z_p, \Phi, Z^*_p)$ remains asymmetric for $y_{in}$=2.4 cm. Similarly, at the $y_{in}$=1.6 cm, particles introduced at lower $\Psi_{in}$ also exit the separator section 116 outside of the viewing area (x<0.5 cm). Therefore, the transfer function is also asymmetric, with non-zero values only at $Z^*_p<Z_p$. In essence, these sub-transfer functions are truncated by the boundaries of the viewing area. As a result, they are not asymmetric, but also appear narrower (e.g., higher sub-resolution). For comparison, at $y_{in}$=2.1 cm, particles introduced along all inlet flow streamlines exit within the viewing area, and the corresponding $P(Z_p, \Phi, Z^*_p)$ is symmetric around $Z_p$.

It is important to note that the contribution of sub-transfer functions truncated by the upper x limit of the viewing area is much greater than those of sub-transfer functions truncated by the lower limit of x for $D_p$ near point C of FIG. 14. For example, the effective $y_{in}$ range for 250 nm particles spans from the center region of the separator section 116 ($y_{in}$=1.56 cm) to the uniform strong electric field region ($y_{in}$=2.97 cm). As the electric field varies rapidly in the center region of the separator section 116, only 250 nm particles introduced within a very narrow range, $1.56 \le y_{in} \le 1.76$ cm, result in an asymmetric $P(Z_p, \Phi, Z^*_p)$, which is truncated by the lower x limit of the viewing area and skewed towards larger $Z^*_p$. In contrast, for 250 nm particles introduced within a relatively large $y_{in}$ region, $2.31 \le y_{in} \le 2.97$ cm, where the electric field is nearly constant and is the strongest, their sub-transfer functions are truncated by the upper x limit. It is noted that 250 nm particles introduced within $2\ 31 \le y_{in} \le 2.97$ also have large values of $x^*_{out}$, corresponding to narrow sub-transfer functions and high sub-resolutions shown in FIG. 12. These sub-transfer functions are further narrowed due to the truncation by the upper x limit, and are asymmetric and skewed towards smaller $Z^*_p$.

Due to the large contribution of these sub-transfer functions, the overall $P(Z_p, Z^*_p)$ is significantly skewed towards smaller $Z^*_p$. The skewed $P(Z_p, Z^*_p)$ has a very narrow width at its half maximum compared to its overall spread in $Z^*_p$ as shown in FIG. 15. Such a feature is only found for particles ranging from 247 nm to 256 nm diameter. This leads to the sharp peak of $R_{FWHM}$ observed at 250 nm diameter. In contrast, $R_{std}$ takes into account the overall spread of the skewed transfer function, and its peak is more gradual compared to that of $R_{FWHM}$ near Point C in FIG. 14. The truncation of sub-transfer function also explains the increases of both $R_{std}$ and $R_{FWHM}$ as particle increases from 380 nm (Point D in FIG. 14). As $D_p$ approaches the upper limit of measurement range, particle effective $y_{in}$ range is limited to the uniform strong electric field region, and the $x^*_{out}$ of particles deceases to near the lower limit of the viewing area (e.g., x=0.5 cm for configuration 2). The positions of these particles at the exit of separator section 116 are shown at area E in FIG. 9. The truncation of sub-transfer function by the lower x limit leads to the artificially high $R_{std}$ and $R_{FWHM}$ near the upper limit of the measurement range shown in FIG. 14.

At the lower limit of the measurement range, $R_{std}$ and $R_{FWHM}$ also show high values for the similar reason described above. For particles near the lower limit of measurement range, due to their high electrical mobilities, only particles introduced within the uniform weak electric field region are detected within the viewing area. These particles exit the separator near the second plate electrode 128 and have higher $x^*_{out}$ as shown at area A FIG. 9, leading to higher $R_{std}$ and $R_{FWHM}$. In addition, for particles near the lower limit of measurement range, the truncation of sub-transfer function by the upper x limit of the viewing area also contributes to the high resolutions shown in FIG. 14. As $D_p$ increases from the lower limit (Point A in FIG. 14), the $x^*_{out}$ of particles introduced within the uniform weak electric field region, which represents a large fraction of the effective $y_{in}$ range, decreases. This leads to decreases in overall resolutions with increasing $D_p$.

For configuration 2, both $R_{std}$ and $R_{FWHM}$ reach their local minimums at $D_p$ of 13 nm (point B in FIG. 14), where $\eta$ also reaches its first peak. As discussed earlier, the effective $y_{in}$ range at 13 nm includes the entire uniform weak electric field region within the viewing area ($-3 \le y_{in} \le -2.4$ cm) in addition to a section within the region with exponentially varying electric field (e.g., $-2.4 \le y_{in} \le -2.04$ cm). Particles with $D_p$ of 13 nm introduced within the uniform weak electric field region have low values of $x^*_{out}$ (e.g., close to the 0.5 cm lower limit of the viewing area), and therefore lower sub-resolutions. Due to the large contribution of these particles, the overall $R_{std}$ and $R_{FWHM}$ at 13 nm are generally lower than those of larger particles detected mainly within the center region with exponentially varying electric field. This leads to the local minimums in both $R_{std}$ and $R_{FWHM}$ shown in FIG. 14.

Counting Statistics

In the previous section, it was shown that WSR-FIMS system 100 can simultaneously measure particles ranging from 10 to 1470 nm (in configuration 1). Due to the fast response of WSR-FIMS system 100, the counting statistics of WSR-FIMS system 100 may limit the maximum frequency with which statistically significant measurements can be obtained. Counting statistics measurements obtained using WSR-FIMS system 100 are discussed below.

For each size bin, the uncertainty ($\sigma_C$) in particle counts measured by WSR-FIMS system 100 can be approximated, based on Poisson statistics, as $\sigma_C = \sqrt{C}$, where C is the number of particle counts detected in the size bin. C can be estimated as described by equation (22) below:

$$C \approx Q_a t_c \eta_{chg} \eta \Delta N = Q_a t_c \eta_{chg} \eta \left( \frac{dN}{d\ln D_p} \right) \Delta \ln D_p \qquad (22)$$

where $t_c$ is the sampling time, $\eta_{chg}$ the fraction of particle carrying one positive charge in a bipolar charger, and N is the particle number concentration. The signal-to-noise ratio is given by $C/\sqrt{C} = \sqrt{C}$. For each decade of particle diameter, particles are grouped into 15 size bins that are evenly spaced on logarithmic scale, and the corresponding bin width $\Delta \ln D_p$ is $\ln(10)/15$. This results in 33 size bins from 10 to 1470 nm in configuration 1 and 25 size bins from 9 to 408 nm in configuration 2, respectively.

Figure 17:
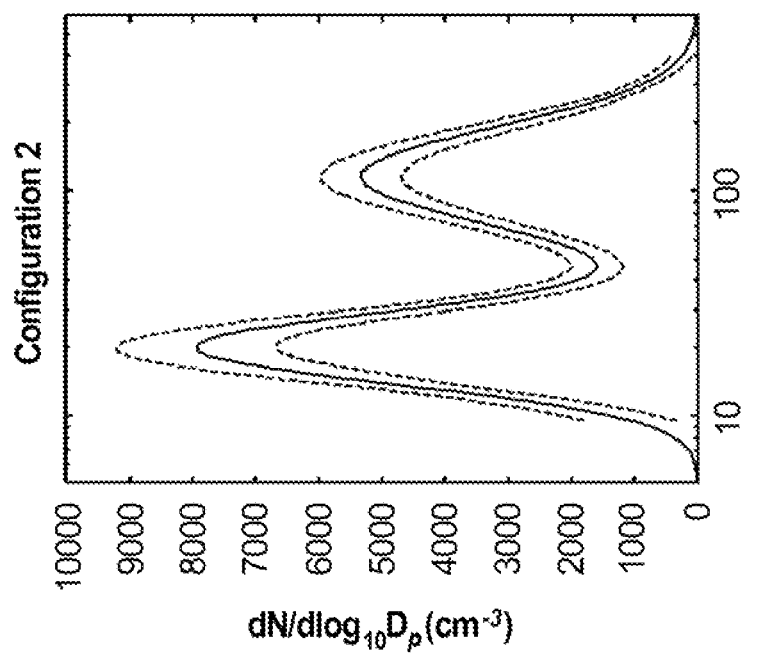
FIG. 17 illustrates a graph of simulated counting statistics of measurements by the WSR-FIMS system of FIG. 1 in accordance with the second configuration.
Figure 16:
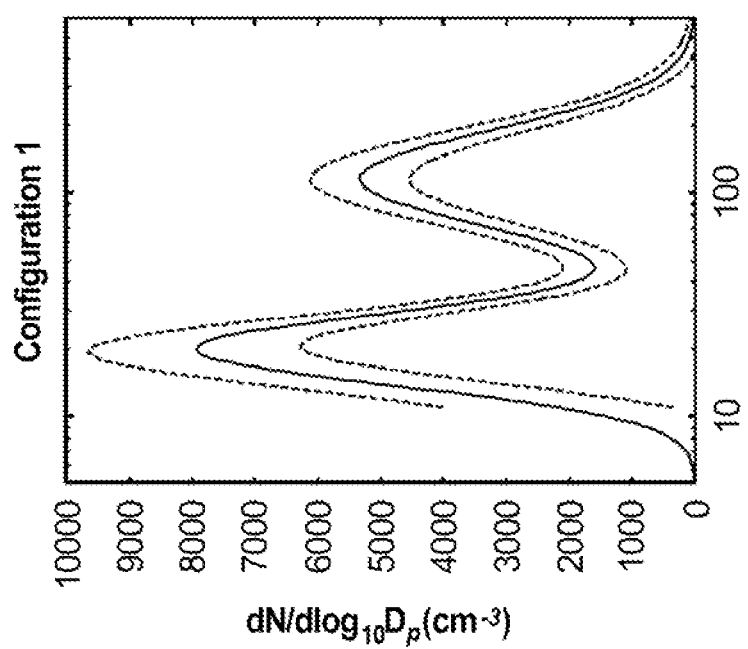
FIG. 16 illustrates a graph of simulated counting statistics of measurements by the WSR-FIMS system of FIG. 1 in accordance with the first configuration.

FIG. 16 illustrates simulated counting statistics of measurements by the WSR-FIMS system 100 of FIG. 1 in accordance with configuration 1. FIG. 17 illustrates simulated counting statistics of measurements by the WSR-FIMS system 100 of FIG. 1 in accordance with configuration 2. The measurement counting statistics derived using equation (22) above. For typical remote continent aerosols, 1 second measurement time is sufficient for WSR-FIMS system 100 to obtain good counting statistics under both configurations. Configuration 2 shown in FIG. 17 has a better counting statistics but a narrower size range compared to configuration 1 shown in FIG. 16. We note that the WSR-FIMS can be operated at a variety of configurations besides the two configurations presented here. For example, increasing the $Q_a$ while maintaining the same $Q_{sh}$ and other parameters leads to improved counting statistics at the expense of reduced size resolution. Such configuration may be used for measurements of ambient aerosols with lower concentrations and boarder distributions. Depending on the characteristics of aerosol, the operation configuration can be optimized to reach the balance among measurement size range, size resolution, and counting statistics.

Effects of Particle Brownian Diffusion on Transfer Function and Resolution

Although detailed characterization of the effect of particle Brownian diffusion on resolution of the WSR-FIMS system 100 will be a subject of future study, a first-order analysis based on migration Peclet number (Pe) is presented below. The migration Peclet number is defined as the ratio of the flux due to electrophoretic migration to that due to diffusion as characterized by equation (23) below:

$$Pe_{mig} = \frac{qV}{kT} \quad (23)$$

In the WSR-FIMS system 100, the voltage applied to the second plate electrode 128 ranged from 27.9 to 11250 volts. Even at the lowest voltage of 27.9 volts, $Pe_{mig}=1086 \gg 1$, suggesting the effect of diffusion is small. At the same ratio of sheath to aerosol flow rate ($Q_{sh}/Q_a$), the resolution of is mainly a function of classifying voltage, and nearly independent of the WSR-FIMS system 100 geometry. The characteristic voltage below which the particle diffusion becomes dominant of the transfer function is shown in equation (24) below:

$$V_{diff} = \frac{0.2 \cdot (1.84 + 2.89\beta)}{\beta^2} \quad (24)$$

where (β is the ratio of $Q_a$ to $Q_{sh}$. $V_{diff}$ varies very little for different geometries. For configuration 2 of the WSR-FIMS system 100, the $x^*_{out}$ of measured particles are limited by the viewing are from 0.5 cm to 0.87 cm, which corresponds to $\beta_x(Q_a/Q_{sh}(x^*_{out}))$, ranging from 0.2 to 0.1. Applying $V_{diff}$ derived using equation (24) to the geometry of the WSR-FIMS system 100, $V_{diff}$ ranges from 12.1 V at $x^*_{out}$=0.5 cm to 43.8 V at $x^*_{out}$=0.87 cm. It is noted that because the voltage applied to the second plate electrode 128 ranges from 27.9 to 11250 volts, it is expected that for nearly the entire measurement size range of configuration 2, particle diffusion does not significantly degrade the sub-resolution or therefore the overall resolution.

For configuration 1, $x^*_{out}$ is limited by the viewing area from 0.20 cm to 0.87 cm, and the corresponding $\beta_x$ ranges from 0.2 to 0.021. $V_{diff}$ derived using equation (24) increases from 12.1 V at $x^*_{out}$=0.2 cm to 862 V at $x^*_{out}$=0.87 cm. For particles that exit separator section 116 with low $x^*_{out}$, which corresponds to a low $V_{diff}$, the sub-transfer function and sub-resolution are not affected significantly for the entire measurement size range of configuration 1. For small particles that exit the separator section 116 in the region with weak electric field, it is expected that the sub-resolution associated with high $x^*_{out}$ will be reduced after particle diffusion is taken into consideration. The stronger impact of diffusion on resolution for configuration 1 is due to its higher non-diffusing sub-resolution, which is up to about 50 as shown in FIG. 11. In contrast, the non-diffusing sub-resolution is mostly less than 12 for configuration 2. Nevertheless, even after particle Brownian diffusion is taken into account, the overall resolution of configuration 1 can only be higher than that of configuration 2, which is nearly identical to the resolution of the typical SMPS as shown in FIG. 14.

Thus, a wide size range fast integrated mobility spectrometer (WSR-FIMS) system has been described. The WSR-FIMS utilizes a non-uniform electric field that varies over three orders of magnitude along the width of the separator section 116, creating regions with different electric field strengths such that particles of a much wider size range can be classified and measured simultaneously. A framework has been developed to derive the transfer function, resolution, and transmission efficiency of the WSR-FIMS system 100. Two representative operation configurations were simulated, and the results demonstrate that the WSR-FIMS system 100 increases the dynamics size range to between about 10 nm and 1470 nm, while achieving higher size resolution than typical SMPS system over nearly the entire measurement size range. The WSR-FIMS system 100 measures particles of different sizes simultaneously and captures the entire size distribution within 1 second or less. For typical ambient aerosol, the simulations indicate that 1 s measurements using the WSR-FIMS system 100 provide good counting statistics.

Although specific example embodiments have been described, it will be evident that various modifications and changes can be made to these embodiments without departing from the broader scope of this application. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural substitutions and changes can be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention, inventive concept or embodiment. Thus, although specific embodiments have been illustrated and described herein, it should be appreciated that any arrangement calculated to achieve the same purpose can be substituted for the specific embodiments shown. This application is intended to cover any and all adaptations or variations of various embodiments. Combinations of the above embodiments and other embodiments, not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features can be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

The invention claimed is:

1. A mobility spectrometer to measure a nanometer particle size distribution, said mobility spectrometer comprising:

a conduit configured to receive and provide fluid communication of a fluid stream having a charged nanometer particle mixture, said conduit including:

a separator section configured to generate an electrical field in two dimensions transverse to a dimension associated with the flow of said charged nanometer particle mixture through said separator section to spatially separate charged nanometer particles of said charged nanometer particle mixture within said two dimensions and where said electrical field along said separator section is non-uniform in at least a first dimension of said two transverse dimensions; and
a detector disposed downstream of said conduit to detect said spatially-separated nanometer particles.

2. The mobility spectrometer of claim 1, wherein said conduit further includes:
a condenser section located between said separator section and said detector configured to condense a condensing agent added to said charged nanometer particle mixture and to grow said spatially-separated nanometer particles.

3. The mobility spectrometer of claim 2, wherein said condenser section is electrically insulated from said separator section.

4. The mobility spectrometer of claim 2, wherein said detector is a camera disposed downstream of said conduit configured to capture images of said grown spatially-separated nanometer particles.

5. The mobility spectrometer of claim 1, wherein said separator section includes:
a first wall having a first electrode extending along said first wall; and
a second opposing wall having a second electrode extending along said second opposing wall, said second electrode comprising a plurality of electrical elements configured to generate said electrical field in two dimensions transverse to the dimension associated with the flow of said charged nanometer particle mixture.

6. The mobility spectrometer of claim 5, wherein said transverse electrical field is non-uniform in both transverse dimensions.

7. The mobility spectrometer of claim 5, wherein said plurality of electrical elements further include at least:
a first electrical element extending along said second opposing wall and set to a first voltage; and
a second electrical element extending along said second opposing wall at a distance separated from said first electrical element and set to a second voltage sufficiently different from said first voltage to generate said transverse electrical field.

8. The mobility spectrometer of claim 7, wherein said plurality of electrical elements further include at least:
a third electrical element extending along said second opposing wall at a distance separated from others of said electrical elements and set to a voltage appropriate to enhance said transverse electrical field.

9. The mobility spectrometer of claim 8, wherein said plurality of electrical elements are set to linearly or exponentially varying voltages between said first voltage and said second voltage.

10. A mobility spectrometer system to measure a nanometer particle size distribution, said mobility spectrometer system comprising:
a charger configured to receive a first fluid stream of nanometer particles and to charge said nanometer particles, said charger further configured to direct said first fluid stream of charged nanometer particles into a conduit of a mobility spectrometer;
a mobility spectrometer in fluid communication with said charger, said mobility spectrometer comprising:
a conduit configured to receive and provide fluid communication of at least said first fluid stream, said conduit including:
a separator section configured to generate an electrical field in two dimensions transverse to a dimension associated with the flow of said first fluid stream through said separator section to spatially separate charged nanometer particles of said first fluid stream in said two dimensions and where said electrical field over said separator section is non-uniform in at least a first dimension of said two transverse dimensions; and
a detector disposed downstream of said conduit to detect said spatially-separated nanometer particles.

11. The mobility spectrometer system claim 10, wherein said mobility spectrometer system further comprises:
a saturator configured to saturate a second fluid stream with a condensing agent and to direct said second fluid stream into said conduit of said mobility spectrometer.

12. The mobility spectrometer system claim 11, wherein said mobility spectrometer further comprises:
a condenser section configured to condense said condensing agent and to grow said spatially-separated nanometer particles.

13. The mobility spectrometer system claim 12, wherein said separator section is electrically insulated from said a condenser section.

14. The mobility spectrometer system of claim 12, wherein said detector is a camera disposed downstream of said conduit configured to capture images of said grown spatially-separated nanometer particles.

15. The mobility spectrometer system of claim 10, wherein said separator section includes:
a first wall having a first electrode extending along said first wall; and
a second opposing wall having a second electrode extending along said second opposing wall, said second electrode comprising a plurality of electrical elements configured to generate said electrical field in two dimensions transverse to the dimensions associated with the flow of said first fluid stream.

16. The mobility spectrometer system of claim 15, wherein said transverse electrical field is non-uniform in both transverse dimensions.

17. The mobility spectrometer system of claim 15, wherein said plurality of electrical elements further include at least:
a first electrical element extending along said second opposing wall and set to a first voltage; and
a second electrical element extending along said second opposing wall at a distance separated from said first electrical element and set to a second voltage sufficiently different from said first voltage to generate said transverse electrical field.

18. The mobility spectrometer system of claim 17, wherein said plurality of electrical elements further include at least:
a third electrical element extending along said second opposing wall at a distance separated from others of said electrical elements and set to a voltage appropriate to enhance said electrical field.

19. The mobility spectrometer system of claim 18, wherein said plurality of electrical elements are set at linearly or exponentially varying voltages between said first voltage and said second voltage.

20. The mobility spectrometer system of claim 10, further comprising a computing device operably connected to said detector, said computing device configured to determine concentration and position of said spatially-separated nanometer particles.

21. A method of measuring a nanometer particle size distribution, the method comprising:
flowing a fluid stream having a charged nanometer particle mixture through a conduit of a mobility spectrometer, the conduit including at least a separator section;

applying a transverse non-uniform electrical field in the separator section in at least one of two dimensions transverse to a dimension associated with the flow of the charged nanometer particle mixture through the separator section to spatially separate the charged nanometer particles within the two dimensions;

detecting the spatially-separated nanometer particles.

22. The method of claim 21, further comprising flowing a first fluid stream having a nanometer particle mixture through a charging zone which charges the particles of the nanometer particle mixture and directs the first fluid stream into the conduit of the mobility spectrometer.

23. The method of claim 21, further comprising flowing a second fluid stream through a saturation zone that saturates the second fluid stream with a condensing agent and directs the second fluid stream into the conduit of the mobility spectrometer.

24. The method of claim 23, further comprising growing the spatially-separated nanometer particles by condensing the condensing agent in a condenser section of the conduit.

25. The method of claim 24, wherein detecting includes:
   illuminating the grown spatially-separated nanometer particles; and
   capturing images of the grown spatially-separated nanometer particles.

26. The method of claim 21, wherein applying the transverse electrical field further comprises:
   grounding a first electrode of the separator section, the first electrode extending along a first wall of the separator; and
   applying varying voltages to a plurality of electrical elements of a second electrode of the separator section to generate the transverse electrical field in two dimensions, the second electrode extending along a second opposing wall of the separator section.

27. The method of claim 26, wherein the applying varying voltages to the plurality of electrical elements of the second electrode comprises applying different voltages to different electrical elements of the plurality of electrical elements, including at least:
   applying a first voltage to a first electrical element of the second electrode extending along the second opposing wall; and
   applying a second voltage sufficiently different from the first voltage to generate the transverse electrical field to a second electrical element of the second electrode disposed at a distance separated from the first electrical element and extending along the second opposing wall.

28. The method of claim 27, wherein the applying varying voltages to the plurality of electrical elements of a second electrode further includes:
   applying a voltage appropriate to enhance the transverse electrical field to at least a third electrical element of the second electrode extending along the second opposing wall.

29. The method of claim 28, wherein the applying varying voltages further includes:
   applying a plurality of different voltages to a plurality of different electrical elements of the second electrode, the voltages varying linearly or exponentially between the first voltage and the second voltage.

30. The method of claim 21, further comprising determining the concentration and position of the spatially-separated nanometer particles.

* * * * *